United States Patent
Pliushchev et al.

(10) Patent No.: US 9,284,272 B2
(45) Date of Patent: Mar. 15, 2016

(54) INHIBITORS OF HISTONE METHYLTRANSFERASE G9A

(71) Applicant: AbbVie Inc., North Chicago, IL (US)

(72) Inventors: Marina A. Pliushchev, Vernon Hills, IL (US); Gary G. Chiang, San Diego, CA (US); William N. Pappano, Libertyville, IL (US); Michael R. Michaelides, Libertyville, IL (US); Ramzi F. Sweis, Lake Bluff, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/229,021

(22) Filed: Mar. 28, 2014

(65) Prior Publication Data

US 2015/0274660 A1  Oct. 1, 2015

(51) Int. Cl.
*C07D 209/40* (2006.01)
*C07D 209/96* (2006.01)
*C07D 403/12* (2006.01)

(52) U.S. Cl.
CPC ............ *C07D 209/40* (2013.01); *C07D 209/96* (2013.01); *C07D 403/12* (2013.01)

(58) Field of Classification Search
CPC ... C07D 209/40; C07D 209/96; C07D 403/12
See application file for complete search history.

(56) References Cited

PUBLICATIONS

Suga, et al. Document No. 136:401777, retrieved from CAPLUS; May 28, 2002.*
Terranova, et al. Document No. 128:217284, retrieved from CAPLUS; Mar. 25, 1998.*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Antignano F., et al., "Epigenetic licensing of Th17 and Treg Cell Differentiation (P1197)," The Journal of Immunology, 2013, vol. 190, p. 50.41.
Antignano F., et al., "Methyltransferase G9a Regulates T cell Differentiation during Murine Intestinal Inflammation," Journal of Clinical Investigation, 2014, vol. 124 (5), pp. 1945-1955.
Eliel E. L. et al., Stereochemistry of Organic Compounds, 1994, John Wiley & Sons, Inc. New York, pp. 119-120, 1206.
Huang J., et al., "G9a and Glp Methylate Lysine 373 in the Tumor Suppressor p53," The Journal of Biological Chemistry, 2010, vol. 285 (13), pp. 9636-9641.
IUPAC 1974 Recommendations for Section E, Fundamental Stereochemistry, Pure and Applied Chemistry, 1976, vol. 45, pp. 13-30.
Prescott, Ed., Methods in Cell Biology, vol. XIV, Academic Press, New York, 1976, pp. 33.
Sweis R.F., et al., "Discovery and Development of Potent and Selective Inhibitors of Histone Methyltransferase G9a," ACS Medicinal Chemistry Letters, 2014, vol. 5 (2), pp. 205-209.
Watanabe H., et al., "Deregulation of Histone Lysine Methyltransferases Contributes to Oncogenic Transformation of Human Bronchoepithelial Cells," Cancer Cell International, 2008, vol. 8, p. 15.
Yuan Y., et al., Cell Death & Disease, 2013, vol. 4, pp. 1-8.

* cited by examiner

*Primary Examiner* — Shawquia Jackson
(74) *Attorney, Agent, or Firm* — Changxia Sun

(57) ABSTRACT

Described herein are compounds, pharmaceutical compositions and methods for treating cancer, inflammation, or autoimmune disease in a subject, or for inhibiting histone methyltransferase G9a.

11 Claims, 12 Drawing Sheets

INHIBITORS OF HISTONE METHYLTRANSFERASE G9A

FIELD OF THE INVENTION

The present invention relates to inhibitors of histone methyltransferases G9a and GLP directed to treatment of cancer, inflammation, and autoimmune disease.

BACKGROUND

Histone methyltransferases (HMTs), a class of enzymatic "writers" of epigenetic marks, have recently emerged as targets of potential therapeutic value. They catalyze the methylation of histone lysines and arginines utilizing Sadenosylmethionine (SAM) as the cofactor/methyl-source. This process can result in either the activation or repression of transcription. Dysregulation of methylation at specific histone sites (alterations in the "histone code") has been implicated in many cancers. Hence, targeting HMT activity has been the subject of much investigation in the field of oncology.

One such HMT is Euchromatic histone methyltransferase 2 (EHMT2), also known as G9a. G9a is primarily responsible for the dimethylation of lysine 9 on histone H3 (H3K9). Several reports have highlighted its link to a variety of cancers, including hepatocellular carcinoma, B cell acute lymphoblastic leukemia, and lung cancers.

While small molecule inhibitors of G9a have been reported as early as 2005, their effectiveness has largely been unsuccessful. Accordingly, there is a need in the art for highly specific inhibitors of G9a that have reduced cytotoxicity to non-tumor cells, and can be combined with other known anti-tumor therapies.

SUMMARY

In one aspect, the present invention relates to a compound having a formula of (I):

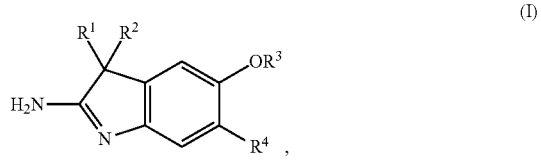

or a pharmaceutically acceptable salt thereof, wherein $R^1$ and $R^2$ are independently selected from the group consisting of hydrogen, alkyl, and haloalkyl, or $R^1$ and $R^2$ together form an optionally substituted 3- to 6-membered cycloalkyl;
$R^3$ is selected from the group consisting of hydrogen, alkyl, alkylalkoxy, alkylamino, and haloalkyl;
$R^4$ is selected from the group consisting of hydrogen, $OR^a$, $SR^a$, $NR^bR^c$, haloalkyl, and alkyl, wherein alkyl is optionally substituted with halogen, haloalkyl, alkyl, aminoalkyl, alkoxy, cycloalkyl, aryl, heterocycle, and heteroaryl, wherein cycloalkyl, aryl, heterocycle, and heteroaryl are optionally substituted with alkyl, halogen, and haloalkyl;
$R^a$ is haloalkyl, cycloalkyl, or alkyl, wherein alkyl is optionally substituted with halogen, haloalkyl, alkyl, amino, aminoalkyl, alkoxy, cycloalkyl, aryl, heterocycle, and heteroaryl, wherein cycloalkyl, aryl, heterocycle, and heteroaryl are optionally substituted with alkyl, halogen, and haloalkyl;
$R^b$ and $R^c$ are each independently haloalkyl, cycloalkyl, or alkyl, wherein alkyl is optionally substituted with halogen, haloalkyl, alkyl, aminoalkyl, alkoxy, cycloalkyl, aryl, heterocycle, and heteroaryl, wherein cycloalkyl, aryl, heterocycle, and heteroaryl are optionally substituted with alkyl, halogen, and haloalkyl; or $R^b$ and $R^c$ together form an optionally substituted 3- to 6-membered heterocycle.

In another aspect, the present invention relates to a method for treating a disease or disorder associated with elevated expression of histone methyltransferase G9a, comprising administration of a therapeutically effective amount of the compound of formula (I) or a pharmaceutically acceptable salt thereof to a subject in need thereof.

In still yet another aspect, the present invention relates to a pharmaceutical composition comprising a therapeutically effective amount of the compound of formula (I) or a pharmaceutically acceptable salt thereof, in combination with one or more pharmaceutically acceptable carriers.

BRIEF DESCRIPTION OF THE DRAWINGS

FIG. 3 is a depiction of the x-ray co-crystal structure of the compound of Example 7 with G9a.

DETAILED DESCRIPTION

Figure 1:
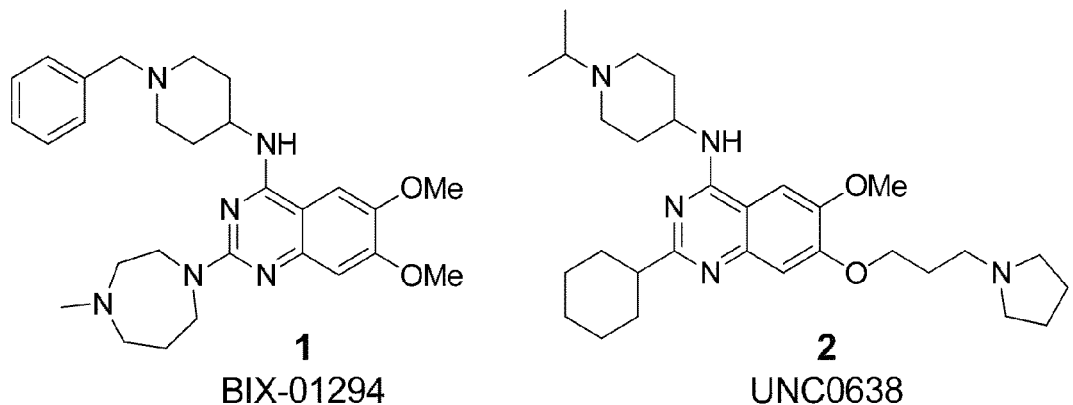
FIG. 1 depicts the chemical structures of known G9a inhibitors, BIX-01294 and UNC0638.

The present invention is directed to an inhibitor of histone methyltransferases G9a and GLP, which have been implicated in a number of different cancers and autoimmune inflammatory disorders including, but not limited to, hepatocellular carcinoma, B cell acute lymphoblastic leukemia, lung cancer and inflammatory bowel diseases. The inhibitors of G9a and GLP as described below are defined by the Formula I. The compound of Formula I has a greater than 1000-fold selectivity for G9a, over other previously known methyltransferases. The compound of Formula I has minimal cytotoxicity on the growth of solid tumor cell lines, but impacts leukemia based tumor cell growth and provides anti-proliferation effects of the same tumor cells. The compound of Formula I may be combined with additive anti-leukemia compounds such as all trans retinoic acid (ATRA) to provide a superior anti-proliferative and reduction in overall leukemic tumor cells.

1. DEFINITIONS

The terminology used herein is for the purpose of describing particular embodiments only and is not intended to be limiting. As used in the specification and the appended claims, the singular forms "a," "an" and "the" include plural references unless the context clearly dictates otherwise.

Section headings as used in this section and the entire disclosure herein are not intended to be limiting.

The terms "administer", "administering", "administered" or "administration" refer to any manner of providing a compound or a pharmaceutical composition (e.g., one described herein), to a subject or patient. Routes of administration can be accomplished through any means known by those skilled in the art. Such means include, but are not limited to, oral, buccal, intravenous, subcutaneous, intramuscular, transdermal, by inhalation and the like.

"Effective amount," as used herein, refers to a dosage of a compound or a composition effective for eliciting a desired effect. This term as used herein may also refer to an amount effective at bringing about a desired in vivo effect in an animal, mammal, or human.

As used herein, the term "inhibit" refers to a reduction or decrease in a quality or quantity, compared to a baseline.

As used herein, the term "subject" is intended to include human and non-human animals. Exemplary human subjects include a human patient having a disorder, or a normal subject. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.).

As used herein, the term "treat" or "treating" a subject having a disorder refers to administering a compound or a composition described herein to the subject, such that at least one symptom of the disorder is cured, healed, alleviated, relieved, altered, remedied, ameliorated, or improved. Treating includes administering an amount effective to alleviate, relieve, alter, remedy, ameliorate, cure, improve or affect the disorder or the symptoms of the disorder. The treatment may inhibit deterioration or worsening of a symptom of a disorder.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkyl" as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" denotes a divalent group derived from a straight or branched chain hydrocarbon containing from 1 to 10 carbon atoms. Representative examples of alkylene include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "amino" refers to a group of the formula —$NR^aR^b$, wherein $R^a$ and $R^b$ are each independently selected from, for example, hydrogen, alkyl, alkenyl, alkynyl, cycloalkyl, heterocycle, aryl and heteroaryl, or $R^a$ and $R^b$, together with the nitrogen to which they are attached, may form a ring structure. Examples of amino groups include but are not limited to —$NH_2$, alkylamino groups such as —$NHCH_3$, —$NHCH_2CH_3$ and —$NHCH(CH_3)_2$, dialkylamino groups such as —$N(CH_3)_2$ and —$N(CH_2CH_3)_2$, and arylamino groups such as —NHPh. Examples of cyclic amino groups include but are not limited to aziridinyl, azetidinyl, pyrrolidinyl, piperidino, piperazinyl, perhydrodiazepinyl, morpholino, and thiomorpholino. The groups $R^a$ and $R^b$ may be optionally substituted with one or more substituents.

The term "alkylamino" as used herein, means at least one amino group, as defined herein, is appended to the parent molecular moiety through an alkylene group, as defined herein.

The term "aminoalkyl" as used herein, means at least one alkyl group, as defined herein, is appended to the parent molecular moiety through an amino group, as defined herein.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system.

The term "halo" or "halogen" as used herein, means Cl, Br, I, or F.

The term "haloalkyl" as used herein, means an alkyl group, as defined herein, in which one, two, three, four, five, six, seven or eight hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heteroaryl" as used herein, means a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heteroatom", as used herein, refers to a non-carbon or hydrogen atom such as a nitrogen, sulfur, oxygen, silicon or phosphorus atom. Groups containing more than one heteroatom may contain different heteroatoms.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "hydroxyl" or "hydroxy" as used herein, means an —OH group.

The term "alkoxy" as used herein, refers to an alkyl group, as defined herein, attached to the parent molecular moiety through an oxygen atom.

The term "alkylalkoxy" as used herein, refers to an alkoxy group, as defined herein, attached to the parent molecular moiety through an alkyl group, as defined herein.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

As used herein, the number of ring atoms in a heterocyclic moiety can be identified by the prefix "$M_x$-$M_y$," where x is the minimum and y is the maximum number of ring atoms in the heterocyclic moiety.

The term "substituents" refers to a group "substituted" on an alkyl, alkenyl, alkynyl, cycloalkyl, heterocycle, aryl, arylalkyl, heteroaryl or heteroarylalkyl group at any atom of that group. Any atom can be substituted. Suitable substituents include, without limitation: acyl, acylamido, acyloxy, alkoxy, alkyl, alkenyl, alkynyl, amido, amino, carboxy, cyano, ester, halo, hydroxy, imino, nitro, oxo (e.g., C=O), phosphonate, sulfinyl, sulfonyl, sulfonate, sulfonamino, sulfonamido, thioamido, thiol, thioxo (e.g., C=S), and ureido. In embodiments, substituents on a group are independently any one single, or any combination of the aforementioned substituents. In embodiments, a substituent may itself be substituted with any one of the above substituents.

The above substituents may be abbreviated herein. For example, the abbreviations Me, Et and Ph represent methyl, ethyl and phenyl, respectively. A more comprehensive list of standard abbreviations used by organic chemists appears in a table entitled Standard List of Abbreviations of the Journal of Organic Chemistry. The abbreviations contained in said list are hereby incorporated by reference.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

As used herein, the term "radiolabel" refers to a compound of the invention in which at least one of the atoms is a radioactive atom or radioactive isotope, wherein the radioactive atom or isotope spontaneously emits gamma rays or energetic particles, for example alpha particles or beta particles, or positrons. Examples of such radioactive atoms include, but are not limited to, $^3$H (tritium), $^{14}$C, $^{11}$C, $^{15}$O, $^{18}$F, $^{35}$S, $^{123}$I and $^{125}$I.

2. ANTI-G9a/GLP COMPOUND

The present invention is directed to a modulator of Euchromatic histone methyltransferase 2, also known as G9a (hereafter "G9a"). The modulator may be a compound that inhibits the dimethylation of lysine 9 on histone H3, by inhibiting G9a, which catalyzes the mono-, di-, and/or trimethylation of lysine. Histone lysine metabolism is associated with epigenetic regulation of the structure of chromatin and gene expression. The compound further inhibits the closely related G9a-like protein, GLP.

The compound of the present invention is notably characterized by high selectivity for G9a, leading to a lack of cytotoxicity in a variety of cells, while still achieving effective inhibition of the cellular target, G9a, and tumor growth inhibition. For example, the compound does not kill peripheral blood mononucleated cells (PBMC), which are a critical component of the immune system. The compound further provides anti-proliferation activity in particular tumor cells such as leukemia tumor cells and can be added with other anti-tumor therapies such as all trans retinoic acid (ATRA). The selectivity feature allows the compound to affect the targeted cellular process without the promiscuity of many anti-cancer compounds known in the art. In addition, the compound does not inhibit protein kinases, despite a structure similar to other known kinase inhibitors. This is also an advantageous feature as it allows the compound of the present invention to selectively bind to G9a without disturbing other vital cell signaling and cell transduction processes.

The compound of the present invention may be a compound of formula (I):

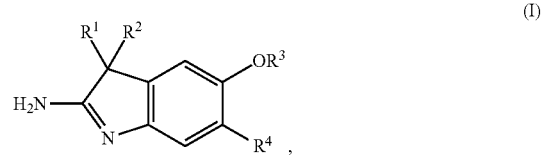

wherein the definitions of $R^1$, $R^2$, $R^3$ and $R^4$ are those found in the Summary.

In one embodiment, $R^1$ and $R^2$ are hydrogen, alkyl, or haloalkyl.

In another embodiment, $R^1$ and $R^2$ are alkyl.

In another embodiment, $R^1$ and $R^2$ together form an optionally substituted 3- to 6-membered cycloalkyl.

In one embodiment, $R^3$ is hydrogen, alkyl, alkylalkoxy, alkylamino, or haloalkyl.

In one embodiment, $R^4$ is hydrogen, $OR^a$, $SR^a$, $NR^bR^c$, haloalkyl, or alkyl, wherein alkyl is optionally substituted with halogen, haloalkyl, alkyl, aminoalkyl, alkoxy, cycloalkyl, aryl, heterocycle, and heteroaryl, and cycloalkyl, aryl, heterocycle, and heteroaryl are optionally substituted with alkyl, halogen, and haloalkyl.

In one embodiment, $R^a$ is haloalkyl, cycloalkyl, or alkyl, wherein alkyl is optionally substituted with halogen, haloalkyl, alkyl, amino, aminoalkyl, alkoxy, cycloalkyl, aryl, heterocycle, or heteroaryl, and wherein cycloalkyl, aryl, heterocycle, and heteroaryl are optionally substituted with alkyl, halogen, or haloalkyl.

In one embodiment, $R^b$ and $R^c$ are haloalkyl, cycloalkyl, or alkyl, wherein alkyl is optionally substituted with halogen, haloalkyl, alkyl, aminoalkyl, alkoxy, cycloalkyl, aryl, heterocycle, or heteroaryl, wherein cycloalkyl, aryl, heterocycle, and heteroaryl are optionally substituted with alkyl, halogen, or haloalkyl.

In another embodiment, $R^b$ and $R^c$ together form an optionally substituted 3- to 6-membered heterocycle.

In one embodiment, $R^4$ is $OR^a$.

In another embodiment, $R^4$ is $OR^a$, and $R^a$ is alkyl optionally substituted with cycloalkyl, heterocycle, or heteroaryl, wherein cycloalkyl, heterocycle, and heteroaryl are optionally substituted with alkyl or halogen.

In another embodiment, $R^4$ is $OR^a$, and $R^a$ is alkyl substituted with heterocycle, wherein the heterocycle is optionally substituted with alkyl or halogen.

In one embodiment, $R^3$ is alkyl, $R^4$ is $OR^a$, and $R^a$ is alkyl optionally substituted with cycloalkyl, heterocycle, or heteroaryl, wherein cycloalkyl, heterocycle, and heteroaryl are optionally substituted with alkyl or halogen.

In another embodiment, $R^3$ is alkyl, $R^4$ is $OR^a$, and $R^a$ is alkyl substituted with heterocycle, wherein the heterocycle is optionally substituted with alkyl or halogen.

In one embodiment, $R^1$ and $R^2$ are alkyl, $R^3$ is alkyl, $R^4$ is $OR^a$, and $R^a$ is alkyl optionally substituted with cycloalkyl, heterocycle, or heteroaryl, wherein cycloalkyl, heterocycle, and heteroaryl are optionally substituted with alkyl or halogen.

In one embodiment, $R^1$ and $R^2$ together form an optionally substituted 3- to 6-membered cycloalkyl, $R^3$ is alkyl, $R^4$ is $OR^a$, and $R^a$ is alkyl optionally substituted with cycloalkyl, heterocycle, or heteroaryl, wherein cycloalkyl, heterocycle, and heteroaryl are optionally substituted with alkyl or halogen.

Specific embodiments contemplated as part of the invention also include, but are not limited to, compounds of Formula (I), as defined, for example:
5',6'-dimethoxyspiro[cyclobutane-1,3'-indol]-2'-amine;
5',6'-dimethoxyspiro[cyclopentane-1,3'-indol]-2'-amine;
5',6'-dimethoxyspiro[cyclohexane-1,3'-indol]-2'-amine;
5'-methoxyspiro[cyclobutane-1,3'-indol]-2'-amine;
5,6-dimethoxy-3H-indol-2-amine;
5'-methoxy-6'-(3-(pyrrolidin-1-yl)propoxy)spiro[cyclobutane-1,3'-indol]-2'-amine;
5'-methoxy-6'-((1-methylpyrrolidin-3-yl)methoxy)spiro[cyclobutane-1,3'-indol]-2'-amine;
5'-methoxy-6'-((1-methylpyrrolidin-2-yl)methoxy)spiro[cyclobutane-1,3'-indol]-2'-amine;
5'-methoxy-6'-(2-(1-methylpyrrolidin-2-yl)ethoxy)spiro[cyclobutane-1,3'-indol]-2'-amine;
6'-(3-(3-fluoroazetidin-1-yl)propoxy)-5'-methoxyspiro[cyclobutane-1,3'-indol]-2'-amine;
6'-(3-(3,3-difluoroazetidin-1-yl)propoxy)-5'-methoxyspiro[cyclobutane-1,3'-indol]-2'-amine;
6'-(3-(1H-imidazol-1-yl)propoxy)-5'-methoxyspiro[cyclobutane-1,3'-indol]-2'-amine;
(S)-6'-(3-(3-fluoropyrrolidin-1-yl)propoxy)-5'-methoxyspiro[cyclobutane-1,3'-indol]-2'-amine;
(R)-6'-(3-(3-fluoropyrrolidin-1-yl)propoxy)-5'-methoxyspiro[cyclobutane-1,3'-indol]-2'-amine;
5-methoxy-3,3-dimethyl-6-(3-(pyrrolidin-1-yl)propoxy)-3H-indol-2-amine; and
6-(3-cyclopentylpropoxy)-5-methoxy-3,3-dimethyl-3H-indol-2-amine.

Compound names are assigned by using Name Release 12.00 v. 12.5 naming algorithm by Advanced Chemical Development or Struct=Name naming algorithm as part of CHEMDRAW® ULTRA v. 12.0

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of the compound may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

On occasion, the relative stereochemistry of an enantiomeric pair is known, however, the absolute configuration is not known. In that circumstance, the relative stereochemistry descriptor terms "R*" and "S*" are used. The terms "R*" and "S*" used herein are defined in Eliel, E. L.; Wilen, S. H. Stereochemistry of Organic Compounds; John Wiley & Sons, Inc.: New York, 1994; pp 119-120 and 1206.

The compound of may exist as a cis or trans isomer, wherein substituents on a ring may attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compound may possess tautomeric forms, as well as geometric isomers, and that these also constitute an aspect of the invention.

The present invention also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

A. Inhibition of G9a Activity

Figure 3:
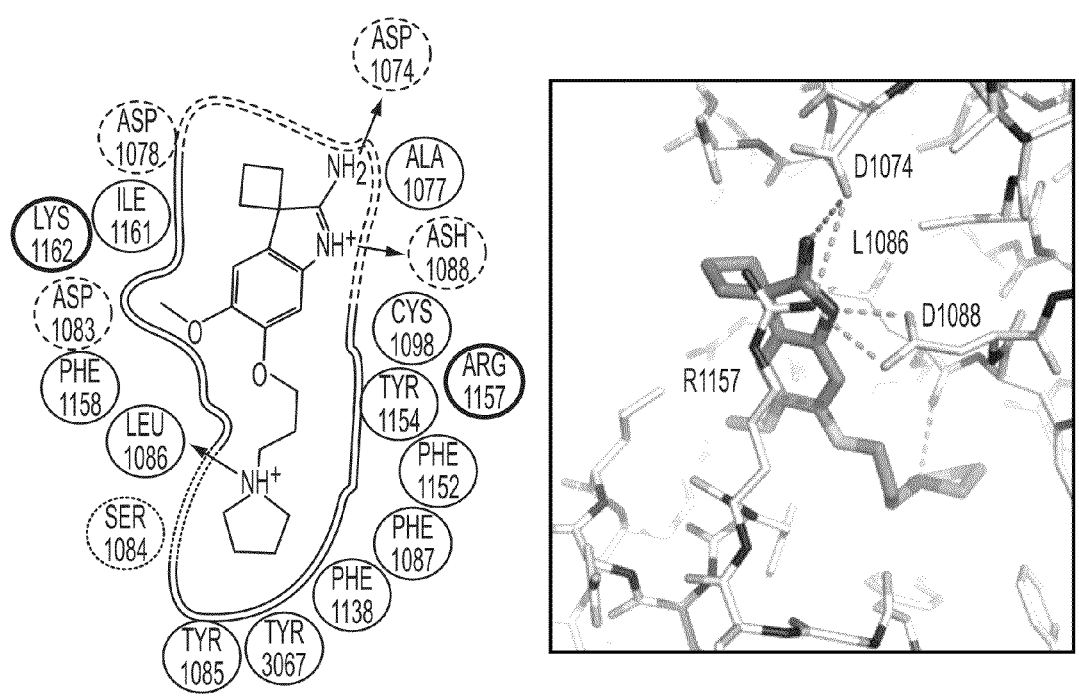

As discussed above, the compound may inhibit G9a's epigenetic regulation of the structures of chromatin and histone methylation. As shown in FIG. 3, the compound may interact with several G9a residues such as Leu 1086, Asp 1088, and Asp 1074 for a strong binding in the active site of G9a.

The compound of formula (I) inhibits G9a with an IC50 ranging from about 1 nM to about 20 uM. The compound may have an IC50 of 20 uM, 19 uM, 18 uM, 17 uM, 16 uM, 15 uM, 14 uM, 13 uM, 12 uM, 11 uM, 10 uM, 9 uM, 8 uM, 7 uM, 6 uM, 5 uM, 4 uM, 3 uM, 2 uM, 1 uM, 900 nM, 800 nM, 700 nM, 600 nM, 500 nM, 400 nM, 300 nM, 200 nM, 100 nM, 90 nM, 80 nM, 70 nM, 60 nM, 50 nM, 45 nM, 40 nM, 35 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.3 nM, 0.2 nM, or 0.1 nM.

As discussed above the compound is notably characterized by high selectivity for G9a, leading to a lack of cytotoxicity in a variety of cells, while still achieving effective inhibition of the cellular target, G9a, and tumor growth inhibition. This feature allows the compound to affect the targeted cellular process without the promiscuity of many anti-cancer compounds known in the art. In addition, the compound does not inhibit protein kinases, despite a structure similar to other known kinase inhibitors. This is also an advantageous feature as it allows the compound of the present invention to selectively bind to G9a without disturbing other vital cell signaling and cell transduction processes. The compound further provides anti-proliferation activity in particular tumor cells such as leukemia tumor cells and can be added with other antitumor therapies such as all trans retinoic acid (ATRA).

The compound of formula (I) inhibits G9a over other known methyltransferases, with greater than 2-fold selectivity, greater than 5-fold selectivity, greater than 10-fold selectivity, greater than 50-fold selectivity, greater than 100-fold selectivity, greater than 200-fold selectivity, greater than 300-fold selectivity, greater than 400-fold selectivity, greater than 500-fold selectivity, greater than 600-fold selectivity, greater than 650-fold selectivity, greater than 700-fold selectivity, greater than 720-fold selectivity, greater than 740-fold selectivity, greater than 760-fold selectivity, greater than 780-fold selectivity, greater than 800-fold selectivity, greater than 820-fold selectivity, greater than 840-fold selectivity, greater than 860-fold selectivity, greater than 880-fold selectivity, greater than 900-fold selectivity, greater than 920-fold selectivity, greater than 940-fold selectivity, greater than 960-fold selectivity, greater than 980-fold selectivity, greater than 1000-fold selectivity, greater than 1020-fold selectivity, greater than 1040-fold selectivity, greater than 1060-fold selectivity, greater than 1080-fold selectivity, greater than 1100-fold selectivity, greater than 1120-fold selectivity, greater than 1140-fold selectivity, greater than 1160-fold selectivity, greater than 1180-fold selectivity, or greater than 1200-fold selectivity.

b. Inhibition of GLP Activity

The compound of formula (I) may further bind to G9a-like protein, GLP, which is capable of dimethylating H3K9 and is also a Euchromatic histone methyltransferase.

The compound of formula (I) inhibits GLP with an IC50 ranging from about 1 nM to about 20 uM. The compound may have an IC50 of 20 uM, 19 uM, 18 uM, 17 uM, 16 uM, 15 uM, 14 uM, 13 uM, 12 uM, 11 uM, 10 uM, 9 uM, 8 uM, 7 uM, 6 uM, 5 uM, 4 uM, 3 uM, 2 uM, 1 uM, 900 nM, 800 nM, 700 nM, 600 nM, 500 nM, 400 nM, 300 nM, 200 nM, 100 nM, 90 nM, 80 nM, 70 nM, 60 nM, 50 nM, 45 nM, 40 nM, 35 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.3 nM, 0.2 nM, or 0.1 nM.

The compound of formula (I) inhibits GLP over other known methyltransferases, with greater than 2-fold selectivity, greater than 5-fold selectivity, greater than 10-fold selectivity, greater than 20-fold selectivity, greater than 30-fold selectivity, greater than 40-fold selectivity, greater than 50-fold selectivity, greater than 60-fold selectivity, greater than 70-fold selectivity, greater than 80-fold selectivity, greater than 90-fold selectivity, greater than 100-fold selectivity, greater than 110-fold selectivity, greater than 120-fold selectivity, greater than 130-fold selectivity, greater than 140-fold selectivity, greater than 150-fold selectivity, greater than 160-fold selectivity, greater than 170-fold selectivity, greater than 180-fold selectivity, greater than 190-fold selectivity, or greater than 200-fold selectivity.

c. General Synthesis

The compound of formula (I) may be prepared by synthetic processes or by metabolic processes. Preparation of the compounds by metabolic processes includes those occurring in the human or animal body (in vivo) or processes occurring in vitro.

The compound of formula (I) may be prepared by a variety of processes that will be understood by one skilled in the art and described in the following Schemes and Examples. For example, the compounds of the present invention wherein the groups $R^1$, $R^2$, $R^3$, and $R^4$ have the meanings as set forth in the Summary of the Invention section unless otherwise noted, can be synthesized as shown in Schemes 1-2.

Abbreviations which have been used in the descriptions of the Schemes that follow are: Bn for benzyl; and HOAc for acetic acid.

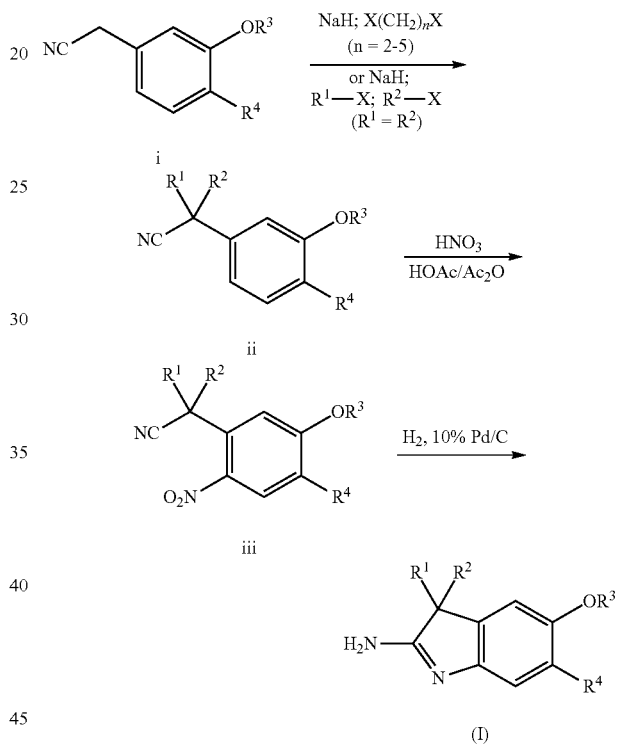

As illustrated in Scheme 1, compounds of formula (I), wherein $R^1$, $R^2$, $R^3$, and $R^4$ are as defined in the Summary of the Invention, can be prepared from the substituted phenylacetonitrile of compound i. Treatment of i with sodium hydride followed by addition of a terminally bis-halogenated alkane, such as 1,3-dibromopropane, can result in alkylation of the benzylic carbon to provide compound ii in which $R^1$ and $R^2$ together form a cycloalkyl ring. Alternatively, a monohalogenated alkane may be used in place of the terminally bis-halogenated alkane in this reaction step to provide compound ii, where $R^1$ and $R^2$ are the same alkyl group. Compound ii can be nitrated with nitric acid to yield the nitrobenzene of compound iii. The nitro group in iii can be reduced under hydrogenation conditions to supply the amino indole compound of formula (I).

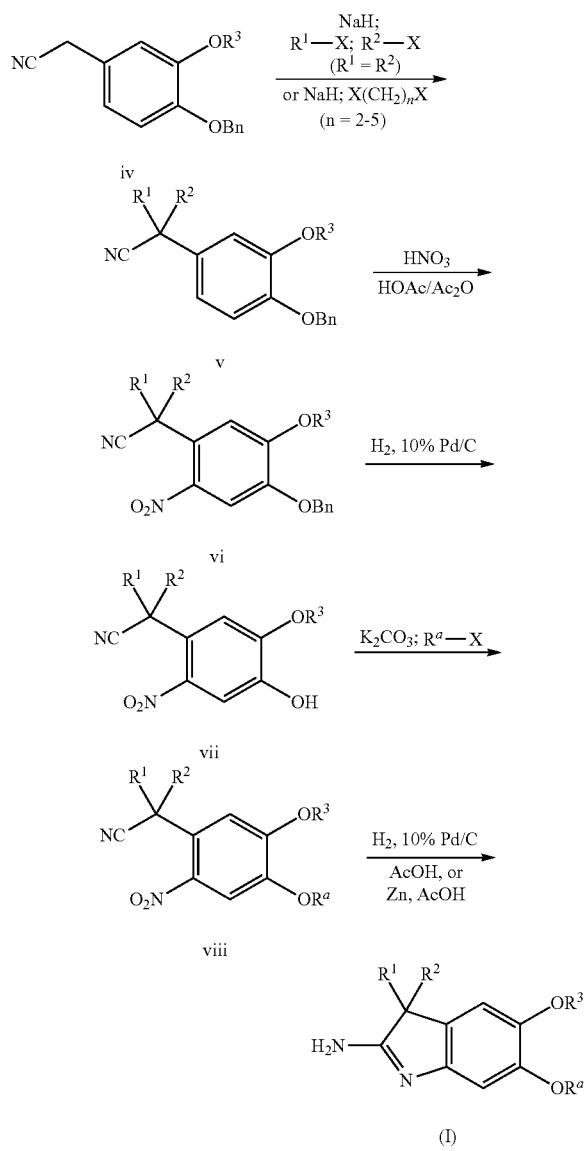

Scheme 2. Alternative Synthesis of the Compound of Formula (I)

In a similar manner, the compound of formula (I), wherein $R^1$, $R^2$, and $R^3$ are as defined in the Summary of the Invention and $R^4$ is $OR^E$, can be synthesized by the alternative route in Scheme 2. Treatment of iv with sodium hydroxide followed by addition of a terminally bis-halogenated alkane, such as 1,3-dibromopropane, can result in alkylation of the benzylic carbon to provide compound v in which $R^1$ and $R^2$ together form a cycloalkyl ring. Alternatively, treatment of iv with sodium hydride followed by addition of a monohalogenated alkane can provide compound v, where $R^1$ and $R^2$ are the same alkyl group. Compound v can be nitrated with nitric acid to yield the nitrobenzene of compound vi. Deprotection of the benzyl ether of vi under hydrogenation conditions can provide compound vii. Subsequent alkylation of the free hydroxyl may provide compound viii. The nitro group of vii can be reduced under hydrogenation conditions to give the amino indole compound of formula (I), wherein $R^4$ is $OR^a$.

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

The compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis ($4^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

4. PHARMACEUTICAL COMPOSITIONS

The present invention is further directed to a pharmaceutical composition comprising the compound of formula (I). The pharmaceutical composition may further comprise one or more pharmaceutically acceptable carrier, and/or adjuvants. The pharmaceutically acceptable carrier is non-toxic. The pharmaceutical compositions can be formulated for any type of administration, including, but not limited to, oral administration in solid or liquid form, for parenteral injection or for topical administration.

The pharmaceutically acceptable carrier may be an inert solid, semi-solid or liquid filler, diluent, encapsulating material or formulation auxiliary of any type.

A. Natural Pharmaceutically Acceptable Carriers

The pharmaceutically acceptable carrier may be a natural or a man-made carrier. A natural pharmaceutical carrier requires no chemical or biological manipulation into a carrier state. Some examples of materials which can serve as natural pharmaceutically acceptable carriers are sugars such as lactose, glucose and sucrose; starches such as corn starch and potato starch; cellulose; powdered tragacanth; malt; gelatin; talc; cocoa butter and suppository waxes; oils such as peanut oil, cottonseed oil, safflower oil, sesame oil, olive oil, corn oil and soybean oil; glycols; agar; alginic acid; pyrogen-free water; isotonic saline; Ringer's solution; ethyl alcohol; phosphate buffer solutions, and antioxidants can also be present in the composition, according to the judgment of one skilled in the art of formulations.

B. Man-Made Pharmaceutically Acceptable Carriers

The pharmaceutically acceptable carrier may be a synthesized man-made carrier. Some examples of synthesized pharmaceutically acceptable carriers may be cellulose derivatives such as sodium carboxymethyl cellulose, ethyl cellulose and cellulose acetate; propylene glycol; esters such as ethyl oleate and ethyl laurate; buffering agents such as magnesium hydroxide and aluminum hydroxide, as well as other nontoxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

C. Administration

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally", as used herein, refers to modes of administration which include intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

1. Rate Releasing Pharmaceutical Compositions

The pharmaceutical composition may be in the form of a rate-releasing composition. In order to prolong the effect of a drug, it is often desirable to slow the absorption of the drug from subcutaneous or intramuscular injection. This may be accomplished by the use of a liquid suspension of crystalline or amorphous material with poor water solubility as a pharmaceutically acceptable carrier with the compound of formula (I). The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compound of formula (I) can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

2. Injection Based Pharmaceutical Compositions

The pharmaceutical composition may be an injection-based formulation. Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

3. Solid Dose Pharmaceutical Compositions

The pharmaceutical composition may be a solid dose formulation. Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and *acacia*; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

4. Suppository Pharmaceutical Compositions

The pharmaceutical composition may be a suppository, Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

5. Liquid Dosage Pharmaceutical Compositions

The pharmaceutical composition may be a liquid dosage form. Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

6. Topical/Transdermal Pharmaceutical Compositions

The pharmaceutical composition may be in the form of a topical or transdermal composition. Dosage forms for topical or transdermal administration of the compound of this formula (I) include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

7. Liposome Pharmaceutical Compositions

The pharmaceutical composition may be in the form of liposomes. As is known in the art, liposomes are generally derived from phospholipids or other lipid substances. Liposomes are formed by mono- or multi-lamellar hydrated liquid crystals that are dispersed in an aqueous medium. Any nontoxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

8. Dosage Forms

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Ophthalmic formulations, eye ointments, powders and solutions are contemplated as being within the scope of this invention. Aqueous liquid compositions comprising compounds of the invention also are contemplated.

9. Pharmaceutically Acceptable Salts

The compound of formula (I) can be used in the form of pharmaceutically acceptable salts or esters, or amides derived from inorganic or organic acids. The term "pharmaceutically acceptable salts and esters and amides", as used herein, refer to carboxylate salts, amino acid addition salts, zwitterions, and esters and amides of compounds of Formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid. An example of a suitable salt is a hydrochloride salt.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Preferred salts of the compounds of the invention are the tartrate and hydrochloride salts.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulfuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, and piperazine.

The term "pharmaceutically acceptable ester", as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$-alkyl esters and $C_5$-to-$C_7$-cycloalkyl esters, although $C_1$-to-$C_4$-alkyl esters are preferred. Esters of the compounds of Formula (I) may be prepared according to conventional methods. For example, such esters may be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also may be prepared by reaction of the compound with an acid such as hydrochloric acid and an alcohol such as methanol or ethanol.

The term "pharmaceutically acceptable amide", as used herein, refers to non-toxic amides of the invention derived from ammonia, primary $C_1$-to-$C_6$-alkyl amines and secondary $C_1$-to-$C_6$-dialkyl amines. In the case of secondary amines, the amine may also be in the form of a 5- or 6-membered heterocycle containing one nitrogen atom. Amides derived from ammonia, $C_1$-to-$C_3$-alkyl primary amides and $C_1$-to-$C_2$-dialkyl secondary amides are preferred. Amides of the compounds of Formula (I) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also may be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The invention contemplates pharmaceutically active compounds either chemically synthesized or formed by in vivo biotransformation to the compound of Formula (I).

5. METHODS OF USING THE COMPOUNDS

The present invention is further directed to methods for treating disorders, diseases, or conditions by inhibiting G9a or GLP using the compound of formula (I) or a pharmaceutical composition as described above (hereafter "the composition"). The methods may include administration of the composition for treatment of disorders or conditions, which can be treated by inhibition of G9a, i.e. the invention relates to the use of such compounds for curative treatment of such a disease or disorder, controlling such a disease or disorder, ameliorating the symptoms associated with such a disease or disorder and reducing the risk for such a disease or disorder.

The composition can be administered to a subject in need thereof to modify histones post-translationally, in particular histone lysine methylation, for a variety of diverse biological processes. The present invention is directed to methods for administering the composition to inhibit G9a, an important mediator of epigenetic gene regulation that is among the histone methyltransferases that are responsible for the dimethylation of lysine 9 on histone H3 (H3K9).

The composition may be useful for treating and preventing certain diseases and disorders in humans and animals related to G9a methylation. Typically, treatment or prevention of such diseases and disorders can be effected by selectively modulating G9a in a subject, by administering a compound or composition of the invention, either alone or in combination with another active agent as part of a therapeutic regimen to a subject in need thereof.

The composition can be administered to a subject to inhibit G9a or GLP related diseases or disorders. The subject can be a mammal. The mammal can be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

The composition can be between 1 µg to 10 mg active component/kg body weight/time and can be 20 µg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The pharmaceutical doses for effective treatment can be 1, 2, 3, 4, 5, 6, 7, 8, 9, 10, or more doses.

A. Method of Treating Cancer with the Compound of Formula I or Pharmaceutical Composition of Formula I The composition can be used to inhibit the G9a or GLP methylation pathway as described above, which is reactive or directed to a cancer or tumor (e.g., melanoma, head and neck, cervical, liver, prostate, blood cancers, esophageal squamous, gastric) of the mammal or subject in need thereof. The inhibition of G9a can lead to treatment and reduction of cancer or tumor growth, and/or reduce metastasis of cancerous or tumor cells. Accordingly, the composition can be used in a method that treats and/or prevents cancer or tumors in the mammal or subject administered the composition to a subject in need thereof. The method can treat cancer or tumor based growth in any type of cancer such as, but not limited to, melanoma, blood cancers (e.g., leukemia, lymphoma, myeloma, B cell acute lymphoblastic leukemia, hepatocellular carcinoma, B cell chronic lymphocytic lymphoma), lung carcinomas, esophageal squamous cell carcinomas, bladder cancer, colorectal cancer, esophagus, gastric cancer, hepatocarcinoma, head and neck, brain, anal cancer, non-small cell lung carcinoma, pancreatic cancer, synovial carcinoma, prostate cancer, testicular cancer, liver cancer, cervical cancer, recurrent respiratory papillomatosis, skin cancer, multiple myeloma, astrocytoma, and stomach cancer.

In some embodiments, the administered composition to a subject in need thereof can mediate reduction, clearance or prevention of additional growth of tumor cells by inhibiting G9a or GLP methylation thereby reducing growth/proliferation of tumor cells (such as myeloma cells), but does not have an effect on immune cells such as polymorphonuclear neutropholic leukocytes, T cells, and B cells.

In some embodiments, the administered composition can increase tumor free survival, reduce tumor mass, slow tumor growth, increase tumor survival, or a combination thereof in the subject. The administered composition can reduce tumor volume by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% in the subject in need thereof. The administered composition can increase tumor free survival 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, and 70% in the subject after administration of the composition.

In some embodiments, the composition can be administered to clear or eliminate the cancer or tumor expressing the one or more oncogenes without damaging or causing illness or death in the subject administered the composition. The composition dose can be between 1 µg to 10 mg active component/kg body weight/time and can be 20 µg to 10 mg component/kg body weight/time. The composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of composition doses for effective treatment can be 1, 2, 3, 4, 5, 6, 7, 8, 9, or 10.

The ability of the compounds of the invention, including, but not limited to, those specified in the examples, to treat B cell acute lymphoblastic leukemia, hepatocellular carcinoma, colon carcinoma, melanoma, prostate carcinoma, ovarian adenocarcinoma, B cell chronic lymphocytic leukemia, multiple myeloma, astrocytoma, and head and neck cancer may be demonstrated by Huang, J. et al. *J. Biol. Chem.* 2010, 285, 9636-9641. Huang and coworkers demonstrate that the tumor suppressor p53 is post-translationally methylated by G9a in a negative manner, maintaining p53 in an inactive state. Overexpression of G9a, in turn, leads to constitutive methylation and underactive p53. Underactive, or inactive p53 is an oncogenic state and leads to proliferation of cancer cells. Huang and coworkers further demonstrate that overexpression of G9a is consistent with all of these cancer types.

The ability of the compounds of the invention, including, but not limited to, those specified in the examples, to treat pancreatic adenocarcinoma may be demonstrated by Yuan, Y. et al. Cell Death & Disease, 2013, 4, 1-8. Yuan and coworkers report enhanced cytotoxicity of a G9a inhibitor in a p53 mutant pancreatic cancer cell line (PANC-1) in combination with an autophagy inducing compound.

The ability of the compounds of the invention, including, but not limited to, those specified in the examples, to treat lung cancer may be demonstrated by Watanabe, H. Et al. *Cancer Cell Int.* 2008, 8:15. Watanabe and coworkers demonstrated that suppression by SiRNA of G9a that is overexpressed in immortalized and transformed cells led to reduced cell proliferation and less anchorage-independent colony growth. Watanabe also showed that suppression of H3K9 and G9a induced apoptosis.

The method for treating cancer as described above may further be combined with other anti-tumor/cancer therapies. The composition, for example, may be combined with anti-retinoic trans acid for treatment of cancer tumors.

B. Method of Treating Inflammatory Disorders

The composition can be used to inhibit the G9a or GLP methylation pathway as described above, which is reactive or directed to an inflammation or autoimmune disease or disorder of the mammal or subject in need thereof. The inhibition of G9a can lead to treatment and reduction of inflammation. Accordingly, the composition can be used in a method that treats and/or prevents inflammation in the mammal or subject administered the composition to a subject in need thereof. The method can treat inflammation, inflammatory bowel disease, ulcerative colitis, Crohn's disease, and autoimmune disease.

In some embodiments, the administered composition to a subject in need thereof can mediate reduction, clearance or prevention of inflammation by inhibiting G9a or GLP methylation thereby reducing inflammation, but not have an effect on immune cells such as polymorphonuclear neutropholic leukocytes, T cells, and B cells.

In some embodiments, the administered composition can reduce inflammation by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% in the subject in need thereof.

In some embodiments, the composition can be administered to reduce inflammation without damaging or causing illness or death in the subject administered the vaccine. The composition dose can be between 1 μg to 10 mg active component/kg body weight/time and can be 20 μg to 10 mg component/kg body weight/time. The composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of composition doses for effective treatment can be 1, 2, 3, 4, 5, 6, 7, 8, 9, or 10.

The ability of the compounds of the invention, including, but not limited to, those specified in the examples, to treat inflammatory bowel disease may be demonstrated by Antignano, F. et al. Journal of Immunology, 2013, 190, 50.41. G9a-mediated dimethylation of H3K9 has been demonstrated to restrict $T_H17$ and $T_{reg}$ cell differentiation in vivo and in vitro, whereas inhibition of G9a activity in wild type T cells promoted $T_H17$ and $T_{reg}$ cell differentiation. Antignano and coworkers demonstrate that G9a-dependent H3K9 is a homeostatic epigenetic checkpoint that licenses $T_H17$ and $T_{reg}$ cell responses by limiting chromatin accessibility and responsiveness to TGFβ1, and that G9a provides a therapeutic target to treat intestinal inflammation.

C. General Dosage Regimes

The composition may be used to treat disorders as described above with the following dosage regimens. Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt or ester, or amide form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

For treatment or prevention of disease, the total daily dose of the compounds of this invention administered to a human or lower animal may range from about 0.0003 to about 100 mg/kg/day. For purposes of oral administration, more preferable doses can be in the range of from about 0.0003 to about 30 mg/kg/day. If desired, the effective daily dose can be divided into multiple doses for purposes of administration; consequently, single dose compositions may contain such amounts or submultiples thereof to make up the daily dose.

D. Combination Therapies

The composition comprising the compound of Formula I as described above may be used in combination with one or more other drugs in the treatment, prevention, control, amelioration, or reduction of risk of diseases or conditions for which the composition or the other drugs may have utility as described above, where the combination of the drugs together are safer or more effective than either drug alone. Such other drug(s) may be administered, by a route and in an amount commonly used therefore, contemporaneously or sequentially with the composition. When a compound of Formula I is used contemporaneously with one or more other drugs, a pharmaceutical composition in unit dosage form containing such other drugs and the compound of formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I. The above combinations include combinations of a compound of the present invention not only with one other active compound, but also with two or more other active compounds. For example, the compound of Formula I can be combined with a variety of different anti-cancer drugs such as chemotherapeutics, anti-tumor agents, and anti-proliferative agents.

Further, the compound of Formula I can be combined with the following, but not limited to, actinomycins, alkylating agents, anthracyclines, antifolates, antiestrogen agents, antimetabolites, anti-androgens, antimicrotubule agents, aromatase inhibitors, bleomycins, $Ca^{2+}$ adenosine triphosphate (ATP)ase inhibitors, cytosine analogs, deltoids/retinoids, dihydrofolate reductase inhibitors, deoxyribonucleic acid (DNA) topoisomerase inhibitors, dopaminergic neurotoxins, glucocorticoids, histone deacetylase inhibitors, hormonal therapies, immunotherapeutic agents, inosine monophosphate (IMP) dehydrogenase inhibitors, isoprenylation inhibitors, luteinizing hormone-releasing hormone agonists, mammalian target of rapamycin (mtor) inhibitors, multi-drug resistance (MDR) inhibitors, mitomycins, photodynamic therapies, proteasome inhibitors, platinum containing compounds, radiation, receptor tyrosine kinase inhibitors, ribonucleotide reductase inhibitors, thrombospondin mimetics, uracil analogs, *vinca* alkaloids, and vitamin D3 analogs such as, but not limited to, γ-radiation or an additional chemotherapeutic agent or additional chemotherapeutic agents such as N-Ac-Sar-Gly-Val-D-alloIle-Thr-Nva-Ile-Arg-Pro-NHCH2CH3 or a salt thereof, actinomycin D, AG13736, alisertib, 17-allylamino-17-demethoxygeldanamycin, 9-aminocamptothecin, N-(4-(3-amino-1H-indazol-4-yl)phenyl}-N'-(2-fluoro-5-methylphenyl)urea or a salt thereof, N-(4-(4-aminothieno[2,3-d]pyrimidin-5-yl)phenyl}-N'-(2-fluoro-5-(trifluoromethyl)phenyl)urea or a salt thereof, anastozole, AP-23573, asparaginase, azacitidine, bevacizurnab, bicalutamide, bleomycin a2, bleomycin b2, bortezemib, busulfan, campathecins, carboplatin, carmustine (BCNU), CB1093, cetuximab, CHOP (C: Cytoxan® (cyclophosphamide); H: Adriamycin® (hydroxydoxorubicin); O: Vincristine (Oncovin®); P: prednisone), chlorambucil, CHIR258, cisplatin, CNF-101, CNF-1001, CNF-2024, CP547632, crisnatol, cytarabine, cyclophosphamide, cytosine arabinoside, daunorubicin, dacarbazine, dactinomycin, dasatinib, daunorubicin, deferoxamine, demethoxyhypocrellin A, depsipeptide, dexamethasone, 17-dimethylaminoethylamino-17-demethoxygeldanamycin, docetaxel, doxifluridine, doxorubicin, EB 1089, epothilone D, epirubicin, 5-ethynyl-1-13-D-ribofuranosylimidazole-4-carboxamide (EICAR), IS erlotinib, etoposide, everolimus, 5-fluorouracil (5-FU), floxuridine, fludarabine, flutamide, gefitinib, geldanamycin, gemcitabine, goserelin, N-(2-(4-hydroxyanilino}-3-pyridinyl}-4-methoxybenzenesulfonamide or a salt thereof, hydroxyurea, idarubicin, ifosfamide, imatinab, interferon-a, interferon-y, IPI-504, irinotecan, KH 1060, lapatanib, leucovorin calcium, LAQ824, leuprolide acetate, letrozole, lomustine (CCNU), lovastatin, megestrol, melphalan, mercaptopurine, methotrexate, 1-methyl-4-phyenylpyridinium, MG132, mitomycin, mitoxantrone, MLN4924, MLN518, MS-275, mycophenolic acid, mitomycin C, nitrosoureas, oprelvekin, oxaliplatin, paclitaxelPD98059, peplomycin, photosensitizer Pc4, phtalocyanine, pirarubicin, plicamycin, prednisone, procarbizine, PTK787, PU24FC1, PU3, radicicol, raloxifene, rapamycin, ratitrexed, retinoids such as pheuretinide, ribavirin, rituximab (Rituxin®), sorafenib, staurosporine, steroids such as dexamethasone and prednisone, suberoylanilide hydroxamic acid, sunitinib, tamoxifen, taxol, temozolamide, temsirolimus, teniposide, thapsigargin, thioguanine, thrombospondin-1, tiazofurin, topotecan, trapoxin, trastuzumab, treosulfan, trichostatin A, trimetrexate, trofosfamide, tumor necrosis factor, valproic acid, vemurafenib, VER49009, verapamil, vertoporfin, vinblastine, vincristine, vindesine, vinorelbine vitamin D3, VX-680, zactima, ZK-EPO, zorubicin or combinations thereof.

Likewise, compounds of the present invention may be used in combination with other drugs that are used in the prevention, treatment, control, amelioration, or reduction of risk of the diseases or conditions for which compounds of the present invention are useful as described above. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds and processes of the invention will be better understood by reference to the following examples, which are intended as an illustration of and not a limitation upon the scope of the invention.

6. EXAMPLES

The present disclosure has multiple aspects, some of which are illustrated by the following non-limiting examples.

Example 1

General Experimental and Analytical Details

The compound of formula (I) was synthesized though various examples as presented below. All reactions were carried out under an atmosphere of nitrogen. Reagents and solvents were used from commercial sources without additional purification. Hydrogenation reactions were run under a balloon. Sample purification was conducted on a Teledyne Isco or Analogix Intelliflash purification system using pre-packed commercially-available silica gel columns. Reverse-phase purification was conducted on a Gilson preparative HPLC using a Phenomenex C18 column and eluting with a gradient of acetonitrile/water in 0.1% TFA. Purity of all final compounds was ≥95% and determined by $^1$H NMR (Varian Inova 400 NMR Spectrometer) and HPLC/MS (Agilent) via the following method:

The gradient was 5% B for 0.1 min, 5-100% B in 5.1 min with a hold at 100% B for 0.5 min then 100-5% B in 0.3 min (2.0 mL/min flow rate). Mobile phase A was 0.1% TFA in water, mobile phase B was HPLC grade MeCN. The column used for the chromatography was a 2.1×50 mm Phenomenex Luna Combi-HTS C8(2) column (5 µm particles) at a temperature of 65° C. Detection methods are diode array (DAD) and evaporative light scattering (ELSD) detection under positive APCI ionization conditions.

$^1$H and $^{13}$C NMR spectra were recorded on a Varian Inova 400 NMR Spectrometer (operating at 400 and 101 MHz respectively). The chemical shifts (δ) reported are given in parts per million (ppm) and the coupling constants (J) are in Hertz (Hz). The spin multiplicities are reported as s=singlet, br. s=broad singlet, d=doublet, t=triplet, q=quartet, dd=doublet of doublet and m=multiplet.

Example 2

5',6'-dimethoxyspiro[cyclohexane-1,3'-indol]-2'-amine

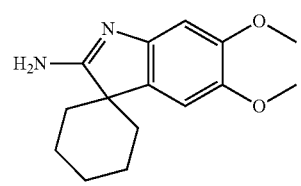 [SMILES: COc1cc2c(cc1OC)C1(CCCCC1)C(N)=N2]

5',6'-Dimethoxyspiro[cyclohexane-1,3'-indol]-2'-amine was generated by the following synthetic sequence of 5 steps.

Step 1

1-(3,4-dimethoxyphenyl)cyclohexanecarbonitrile

A suspension of sodium hydride (0.3 g, 7.5 mmol, 60% dispersion in oil) in THF (9 mL) was cooled to 0° C. and treated slowly with 2-(3,4-dimethoxyphenyl)acetonitrile (0.532 g, 3 mmol) in THF (3 mL). After stirring for 15 min at this temperature 1,5-dibromopentane (0.49 mL, 3.6 mmol) in THF (3 mL) was added, the bath was removed, and the reaction was left stirring at room temperature for 18 h. The reaction was quenched with saturated aqueous ammonium chloride, extracted with EtOAc and washed with brine. The organic layer was dried (MgSO$_4$), filtered and concentrated to provide 1-(3,4-dimethoxyphenyl)cyclohexanecarbonitrile, which was used without further purification in the next step. MS (ESI) m/z 246 (M+H)$^+$.

Step 2

1-(4,5-dimethoxy-2-nitrophenyl)cyclohexanecarbonitrile 1-(3,4-Dimethoxyphenyl)cyclohexanecarbonitrile (0.736 g, 3 mmol), prepared in Step 1, was dissolved in HOAc/Ac$_2$O 1/1 (6 mL) was cooled to 0° C. and treated slowly with nitric acid (0.582 g, 6 mmol, 65%). The reaction was left stirring in the ice bath for 10 min, poured into ice and extracted with EtOAc. Organic layer was dried (MgSO$_4$), filtered and concentrated. Purification by flash chromatography (silica gel, 5-25% EtOAc/hexane) afforded (251 mg, 29%) of 1-(4,5-dimethoxy-2-nitrophenyl)cyclohexanecarbonitrile. MS (ESI) m/z 291 (M+H)$^+$.

Step 3

5',6'-dimethoxyspiro[cyclohexane-1,3'-indol]-2'-amine 1-(4,5-Dimethoxy-2-nitrophenyl)cyclohexanecarbonitrile (0.251 g, 0.865 mmol), prepared in Step 2, in AcOH (6 mL) was treated with 10% Pd/C, fitted with hydrogen balloon and heated to 70° C. for 3 hours under hydrogen atmosphere. The catalyst was filtered off and washed with EtOH. The solvent was concentrated. Purification by reverse phase HPLC afforded 17 mg (8%) of 5',6'-dimethoxyspiro[cyclohexane-1,3'-indol]-2'-amine $^1$H NMR (400 MHz, DMSO) δ 7.11 (s, 1H), 6.64 (s, 1H), 3.72 (s, 3H), 3.70 (s, 3H), 1.88-1.84 (m 4H), 1.82-1.66 (m, 4H), 1.22 (d, J=10.2 Hz, 2H). MS (ESI) m/z 261 (M+H)$^+$.

Example 3

5',6'-dimethoxyspiro[cyclobutane-1,3'-indol]-2'-amine

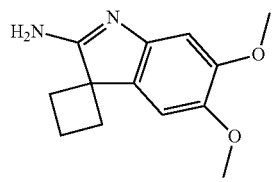 [SMILES: COc1cc2c(cc1OC)C1(CCC1)C(N)=N2]

5',6'-Dimethoxyspiro[cyclobutane-1,3'-indol]-2'-amine was prepared according to the procedure outlined in Example 2 substituting 1,3-dibromopropane for 1,3-dibromopentane in Step 1 of the three-step sequence. $^1$H NMR (400 MHz, DMSO) δ 7.15 (s, 1H), 6.93 (s, 2H), 6.57 (s, 1H), 3.72 (d, J=13.1 Hz, 6H), 2.40-2.24 (m, 1H), 2.24-2.04 (m, 3H). MS (APCI) m/z 233 (M+H)+.

Example 4

5',6'-dimethoxyspiro[cyclopentane-1,3'-indol]-2'-amine

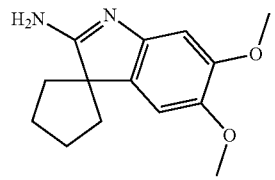 [SMILES: COc1cc2c(cc1OC)C1(CCCC1)C(N)=N2]

5',6'-Dimethoxyspiro[cyclopentane-1,3'-indol]-2'-amine was prepared according to the procedure outlined in Example 2 substituting 1,3-dibromobutane for 1,3-dibromopentane in Step 1 of the three-step sequence. $^1$H NMR (400 MHz, DMSO) δ 6.77 (s, 1H), 6.61 (s, 1H), 3.71 (s, 3H), 3.68 (s, 3H), 1.94 (s, 4H), 1.90 (s, 4H). MS (APCI) m/z 247 (M+H)+.

Example 5

5'-methoxyspiro[cyclobutane-1,3'-indol]-2'-amine

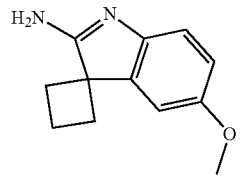

5'-Methoxyspiro[cyclobutane-1,3'-indol]-2'-amine was prepared according to the procedure outlined in Example 2 substituting 1,3-dibromopropane for 1,3-dibromopentane and 2-(3-methoxyphenyl)acetonitrile for 2-(3,4-dimethoxyphenyl)acetonitrile in Step 1 of the three-step sequence. $^1$H NMR (400 MHz, DMSO) δ 11.87 (s, 1H), 10.02 (s, 1H), 9.83 (s, 1H), 7.42 (d, J=2.4 Hz, 1H), 7.05 (d, J=8.5 Hz, 1H), 6.89 (dd, J=8.6, 2.5 Hz, 1H), 3.80 (s, 3H), 2.40-2.24 (m, 1H), 2.24-2.04 (m, 3H). MS (APCI) m/z 203 (M+H)+.

Example 6

5,6-dimethoxy-3H-indol-2-amine

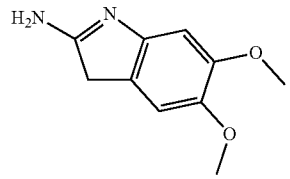

A solution of 2-(4,5-dimethoxy-2-nitrophenyl)acetonitrile (0.22 g, 1 mmol) in ethanol (15 ml) was treated with tin chloride (0.50 g, 2.2 mmol) and heated to 70° C. for 72 hours. The reaction mixture was allowed to cool to room temperature, extracted with EtOAc and washed with 1N NaOH and water. The combined organic extracts were dried over MgSO$_4$, filtered and concentrated. HPLC purification provided 5,6-dimethoxy-3H-indol-2-amine (12 mg, 6.2%). $^1$H NMR (400 MHz, DMSO) δ 11.82 (s, 1H), 9.80 (s, 1H), 9.54 (s, 1H), 7.11 (s, 1H), 6.82 (s, 1H), 4.10 (s, 2H), 3.77 (s, 3H), 3.73 (s, 3H). MS (APCI) m/z 193 (M+H)+.

Example 7

5'-methoxy-6'-(3-(pyrrolidin-1-yl)propoxy)spiro[cyclobutane-1,3'-indol]-2'-amine

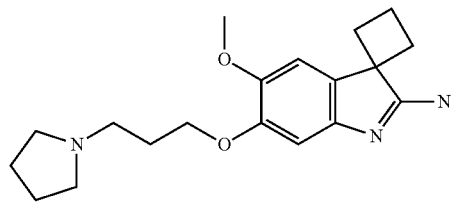 [SMILES: COc1cc2c(cc1OCCCN1CCCC1)N=C(N)C21CCC1]

5'-Methoxy-6'-(3-(pyrrolidin-1-yl)propoxy)spiro[cyclobutane-1,3'-indol]-2'-amine was generated by the following synthetic sequence of 5 steps.

Step 1

1-(4-(benzyloxy)-3-methoxyphenyl)cyclobutanecarbonitrile

To a solution of 2-(4-(benzyloxy)-3-methoxyphenyl)acetonitrile (3.1 g, 12.24 mmol) in dichloromethane (30 mL) was added sodium hydroxide (30 mL, 50% aqueous solution, 367 mmol), TBAB (0.99 g, 3.06 mmol) and then with 1,3-dibromopropane (2 mL, 19.58 mmol). The reaction was stirred at room temperature for 72 hours. The layers were separated, organic layer was dried (MgSO₄) and concentrated. Purification by flash chromatography (silica gel, 5-25% EtOAc/hexane) afforded 1-(4-(benzyloxy)-3-methoxyphenyl)cyclobutanecarbonitrile (1.8 g, 50%). MS (ESI) m/z 294 (M+H)⁺.

Step 2

1-(4-(benzyloxy)-5-methoxy-2-nitrophenyl)cyclobutanecarbonitrile

A solution of 1-(4-(benzyloxy)-3-methoxyphenyl)cyclobutanecarbonitrile (5 g, 17.04 mmol), from Step 1, in acetic acid (20 mL)/acetic anhydride (20 mL) was cooled in an ice bath to 0° C. and treated slowly with 65% nitric acid (2.54 mL, 34.1 mmol). The reaction was stirred at 0° C. for 20 min, poured into ice and extracted with EtOAc. Organic layer was washed with saturated aqueous NaHCO₃ and water. Organic layer was dried (MgSO₄), filtered and concentrated. Purification by flash chromatography (silica gel, 5-50% EtOAc/hexane) afforded 1-(4-(benzyloxy)-5-methoxy-2-nitrophenyl)cyclobutanecarbonitrile (5.29 g, 92%). MS (ESI) m/z 339 (M+H)⁺.

Step 3

1-(4-(hydroxyl)-5-methoxy-2-nitrophenyl)cyclobutanecarbonitrile

A solution of 1-(4-(benzyloxy)-5-methoxy-2-nitrophenyl)cyclobutanecarbonitrile (2.78 g, 8.22 mmol), from Step 2, in EtOH (30 mL) was treated with 10% Pd/C (0.87 g, 0.822 mmol), fitted with hydrogen filled balloon and heated to 70° C. for 3 hours under hydrogen atmosphere. The catalyst was filtered off and washed with EtOH. Solvent was concentrated to provide 1-(4-(hydroxy)-5-methoxy-2-nitrophenyl)cyclobutanecarbonitrile (2 g, 99%). MS (ESI) m/z 249 (M+H)⁺.

Step 4

1-(5-methoxy-2-nitro-4-(3-(pyrrolidin-1-yl)propoxy)phenyl)cyclobutanecarbonitrile To a solution of 1-(4-(hydroxyl)-5-methoxy-2-nitrophenyl)cyclobutanecarbonitrile (0.73 g, 2.93 mmol), from Step 3, in MeCN (20 mL) was added potassium carbonate (1.215 g, 8.79 mmol) and 1-(3-bromopropyl)pyrrolidine hydrochloride (1 g, 4.4 mmol) and stirred at 100° C. for 3 hours. The reaction mixture was concentrated, and extracted with dichloromethane. The combined organic extracts were washed with brine. The organic layer was dried (MgSO₄), filtered and concentrated. Purification by flash chromatography (silica gel, 5-20% methanol/dichloromethane) afforded 0.63 g (59%) of 1-(5-methoxy-2-nitro-4-(3-(pyrrolidin-1-yl)propoxy)phenyl)cyclobutanecarbonitrile. ¹H NMR (400 MHz, METHANOL-D4) δ 7.65 (s, 1H), 6.94 (s, 1H), 4.14 (t, J=6.1 Hz, 2H), 3.97 (s, 3H), 2.87 (ddd, J=8.6, 5.3, 2.5 Hz, 2H), 2.77-2.67 (m, 2H), 2.68-2.52 (m, 6H), 2.42 (dd, J=14.6, 6.3 Hz, 1H), 2.13-2.01 (m, 2H), 2.01-1.89 (m, 1H), 1.84 (dt, J=6.6, 3.2 Hz, 4H). MS (ESI) m/z 360 (M+H)⁺.

Step 5

5'-methoxy-6'-(3-(pyrrolidin-1-yl)propoxy)spiro[cyclobutane-1,3'-indol]-2'-amine A solution of 1-(5-methoxy-2-nitro-4-(3-(pyrrolidin-1-yl)propoxy)phenyl)cyclobutanecarbonitrile (0.063 g, 1.742 mmol), from Step 4, in acetic acid (10 mL), was treated with 10% Pd/C (0.56 g, 0.523 mmol). The mixture was stirred under an atmosphere of hydrogen at 80° C. for 5 hours. The catalyst was filtered off and washed with EtOH. The filtrate was concentrated and resulting crude product was purification by flash chromatography (silica gel, 15-25% 3N methanolic ammonia/dichloromethane) to afford 0.161 g (28%) of 5'-methoxy-6'-(3-(pyrrolidin-1-yl)propoxy)spiro[cyclobutane-1,3'-indol]-2'-amine ¹H NMR (400 MHz, METHANOL-D4) δ 7.28 (s, 1H), 6.71 (s, 1H), 4.11 (t, J=5.7 Hz, 2H), 3.88 (s, 3H), 3.27-3.19 (m, 6H), 2.63 (t, J=9.9 Hz, 2H), 2.52-2.42 (m, 1H), 2.38 (dd, J=13.0, 10.4 Hz, 2H), 2.31-2.22 (m, 1H), 2.17 (dt, J=12.8, 6.2 Hz, 2H), 2.04 (t, J=6.8 Hz, 6H). MS (ESI) m/z 330 (M+H)⁺.

Example 8

5'-methoxy-6'-((1-methylpyrrolidin-3-yl)methoxy)spiro[cyclobutane-1,3'-indol]-2'-amine

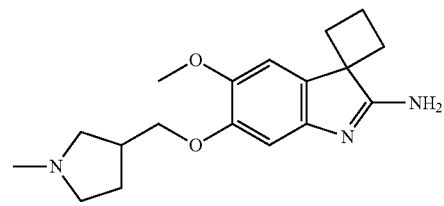 [SMILES: COc1cc2c(cc1OCC1CCN(C)C1)N=C(N)C21CCC1]

5'-Methoxy-6'-((1-methylpyrrolidin-3-yl)methoxy)spiro[cyclobutane-1,3'-indol]-2'-amine was prepared according to the procedure outlined in Example 7 substituting 3-(bromomethyl)-1-methylpyrrolidine for 1-(3-bromopropyl)pyrrolidine hydrochloride in Step 4 of the five-step sequence. MS (ESI) m/z 316 (M+H)⁺.

Example 9

5'-methoxy-6'-((1-methylpyrrolidin-2-yl)methoxy)spiro[cyclobutane-1,3'-indol]-2'-amine

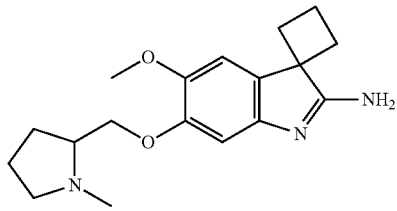 [SMILES: COc1cc2c(cc1OCC1CCCN1C)N=C(N)C21CCC1]

5'-Methoxy-6'-((1-methylpyrrolidin-2-yl)methoxy)spiro[cyclobutane-1,3'-indol]-2'-amine was prepared according to the procedure outlined in Example 7 substituting 2-(bromomethyl)-1-methylpyrrolidine for 1-(3-bromopropyl)pyrrolidine hydrochloride in Step 4 of the five-step sequence. MS (ESI) m/z 316 (M+H)⁺.

Example 10

5'-methoxy-6'-(2-(1-methylpyrrolidin-2-yl)ethoxy)spiro[cyclobutane-1,3'-indol]-2'-amine

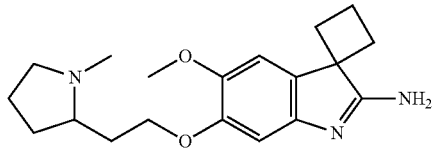 [SMILES: COc1cc2c(cc1OCCC1CCCN1C)N=C(N)C21CCC1]

5'-Methoxy-6'-(2-(1-methylpyrrolidin-2-yl)ethoxy)spiro[cyclobutane-1,3'-indol]-2'-amine was prepared according to the procedure outlined in Example 7 substituting 2-(2-bromoethyl)-1-methylpyrrolidine for 1-(3-bromopropyl)pyrrolidine hydrochloride in Step 4 of the five-step sequence. MS (ESI) m/z 330 (M+H)⁺.

Example 11

6'-(3-(1H-imidazol-1-yl)propoxy)-5'-methoxyspiro[cyclobutane-1,3'-indol]-2'-amine

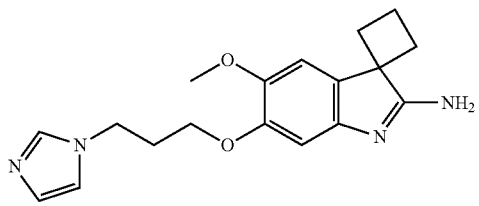 [SMILES: COc1cc2c(cc1OCCCn1ccnc1)N=C(N)C21CCC1]

6'-(3-(1H-Imidazol-1-yl)propoxy)-5'-methoxyspiro[cyclobutane-1,3'-indol]-2'-amine was prepared according to the procedure outlined in Example 6 substituting 1-(3-bromopropyl)-1H-imidazole for 1-(3-bromopropyl)pyrrolidine hydrochloride in Step 4 of the five-step sequence. ¹H NMR (400 MHz, METHANOL-D4) δ 7.93 (s, 1H), 7.18 (s, 2H), 7.01 (s, 1H), 6.47 (s, 1H), 4.18 (s, 2H), 3.76 (s, 3H), 3.58-3.33 (m, 2H), 2.58-2.52 (m, 2H), 2.49-2.35 (m, 1H), 2.34-2.28 (m, 2H), 2.25-2.12 (m, 1H), 2.05-2.00 (m, 2H). MS (ESI) m/z 327 (M+H)⁺.

Example 12

(S)-6'-(3-(3-fluoropyrrolidin-1-yl)propoxy)-5'-methoxyspiro[cyclobutane-1,3'-indol]-2'-amine

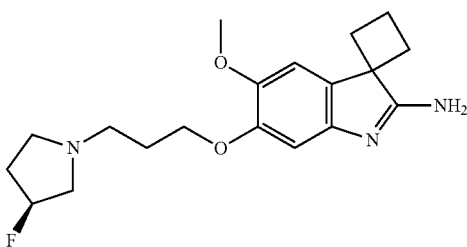 [SMILES: COc1cc2c(cc1OCCCN1CC[C@H](F)C1)N=C(N)C21CCC1]

Step 1

1-(4-(3-chloropropoxy)-5-methoxy-2-nitrophenyl)cyclobutanecarbonitrile

5'-Methoxy-6'-(3-(pyrrolidin-1-yl)propoxy)spiro[cyclobutane-1,3'-indol]-2'-amine was generated by the following synthetic sequence of 5 steps.

Step 1

1-(4-(3-chloropropoxy)-5-methoxy-2-nitrophenyl)cyclobutanecarbonitrile 1-(4-(Hydroxyl)-5-methoxy-2-nitrophenyl)cyclobutanecarbonitrile (0.5 g, 2 mmol) in MeCN (10 mL) was treated with potassium carbonate (0.306 g, 2.2 mmol) and 1-chloro-3-iodopropane (0.425 mL, 4 mmol) and stirred at 80° C. for 3 hours. The reaction mixture was concentrated, extracted with dichloromethane and washed with brine. The organic layer was dried (MgSO₄), filtered and concentrated. Purification by flash chromatography (silica gel, 5-24% EtOAc/hexane) afforded 0.63 g (96%) of 1-(4-(3-chloropropoxy)-5-methoxy-2-nitrophenyl)cyclobutanecarbonitrile. MS (ESI) m/z 325 (M+H)⁺.

Step 2

1-(4-(3-chloropropoxy)-5-methoxy-2-nitrophenyl)cyclobutanecarbonitrile 1-(4-(3-Chloropropoxy)-5-methoxy-2-nitrophenyl)cyclobutanecarbonitrile (0.33 g, 1 mmol), from Step 1, potassium iodide (0.33 g, 2 mmol) and TBAI (0.018 g, 0.05 mmol) were heated in MeCN (4 mL) to 80° C. and treated with potassium carbonate (0.35 g, 2.5 mmol) and (S)-3-fluoropyrrolidine hydrochloride (0.38 g, 3 mmol). The reaction mixture was stirred at 80° C. for 18 hours, filtered and concentrated. Purification by flash chromatography (silica gel, 5-25% methanol/dichloromethane) afforded 0.33 g (88%) of 1-(4-(3-chloropropoxy)-5-methoxy-2-nitrophenyl)cyclobutanecarbonitrile. MS (ESI) m/z 378 (M+H)⁺.

Step 3

(S)-6'-(3-(3-fluoropyrrolidin-1-yl)propoxy)-5'-methoxyspiro[cyclobutane-1,3'-indol]-2'-amine (S)-1-(4-(3-(3-Fluoropyrrolidin-1-yl)propoxy)-5-methoxy-2-nitrophenyl)cyclobutanecarbonitrile (0.332 g, 0.88 mmol) was prepared using the method described in Step 5 of Example 7 to afford (S)-6'-(3-(3-fluoropyrrolidin-1-yl)propoxy)-5'-methoxyspiro[cyclobutane-1,3'-indol]-2'-amine (118 mg, 38%). $^1$H NMR (400 MHz, METHANOL-D4) δ 7.21 (s, 1H), 6.66 (s, 1H), 5.18 (dt, J=55.5, 5.7 Hz, 1H), 4.03 (t, J=6.2 Hz, 2H), 3.84 (s, 3H), 3.04-2.88 (m, 2H), 2.78-2.57 (m, 5H), 2.51-2.39 (m, 2H), 2.39-2.30 (m, 2H), 2.29-2.11 (m, 2H), 2.11-1.95 (m, 3H). MS (ESI) m/z 348 (M+H)$^+$.

Example 13

6'-(3-(3-fluoroazetidin-1-yl)propoxy)-5'-methoxyspiro[cyclobutane-1,3'-indol]-2'-amine

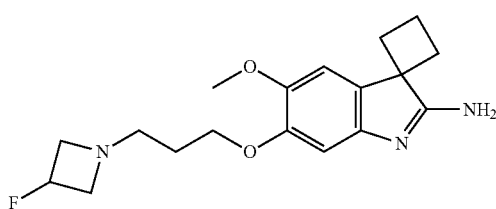 [SMILES: COc1cc2c(cc1OCCCN1CC(F)C1)N=C(N)C21CCC1]

6'-(3-(3-Fluoroazetidin-1-yl)propoxy)-5'-methoxyspiro[cyclobutane-1,3'-indol]-2'-amine was prepared according to the procedure outlined in Example 12, substituting 3-fluoroazetidine for (S)-3-fluoropyrrolidine hydrochloride in Step 2 of the three-step sequence. $^1$H NMR (500 MHz, DMSO) δ 7.45 (s, 1H), 6.77 (s, 1H), 5.37 (d, J=56.1 Hz, 1H), 3.99 (t, J=5.8 Hz, 2H), 3.84 (s, 3H), 2.70 (dd, J=20.6, 9.9 Hz, 2H), 2.55-2.50 (m, 6H), 2.38 (dd, J=20.1, 6.8 Hz, 3H), 2.21 (dd, J=10.5, 5.0 Hz, 1H), 1.92 (d, J=23.1 Hz, 2H). MS (APCI) m/z 334 (M+H)$^+$.

Example 14

6'-(3-(3,3-difluoroazetidin-1-yl)propoxy)-5'-methoxyspiro[cyclobutane-1,3'-indol]-2'-amine

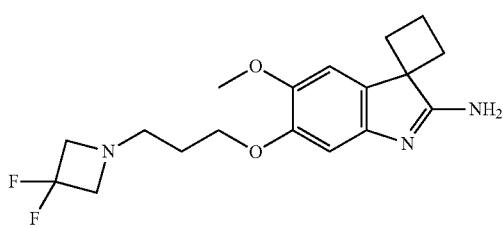 [SMILES: COc1cc2c(cc1OCCCN1CC(F)(F)C1)N=C(N)C21CCC1]

6'-(3-(3,3-Difluoroazetidin-1-yl)propoxy)-5'-methoxyspiro[cyclobutane-1,3'-indol]-2'-amine was prepared according to the procedure outlined in Example 12, substituting 3,3-difluoroazetidine for (S)-3-fluoropyrrolidine hydrochloride in Step 2 of the three-step sequence. $^1$H NMR (400 MHz, METHANOL-D4) δ 7.45 (s, 1H), 6.81 (s, 1H), 4.65-4.55 (m, 4H), 4.20-4.10 (m, 2H), 3.95 (s, 3H), 2.77 (dd, J=19.1, 8.3 Hz, 2H), 2.65-2.49 (m, 3H), 2.38-2.22 (m, 1H), 2.20-2.10 (m, 2H). MS (APCI) m/z 352 (M+H)$^+$.

Example 15

(R)-6'-(3-(3-fluoropyrrolidin-1-yl)propoxy)-5'-methoxyspiro[cyclobutane-1,3'-indol]-2'-amine

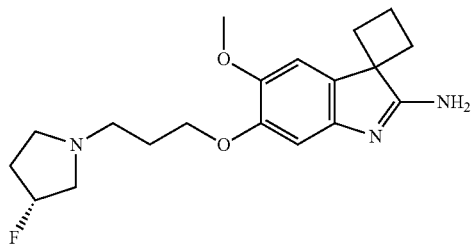 [SMILES: COc1cc2c(cc1OCCCN1CC[C@@H](F)C1)N=C(N)C21CCC1]

(R)-6'-(3-(3-Fluoropyrrolidin-1-yl)propoxy)-5'-methoxyspiro[cyclobutane-1,3'-indol]-2'-amine was prepared according to the procedure outlined in Example 11, substituting (R)-3-fluoropyrrolidine hydrochloride for (S)-3-fluoropyrrolidine hydrochloride in Step 2 of the three-step sequence. $^1$H NMR (400 MHz, METHANOL-D4) δ 7.21 (s, 1H), 6.66 (s, 1H), 5.18 (dt, J=55.5, 5.7 Hz, 1H), 4.03 (t, J=6.2 Hz, 2H), 3.84 (s, 3H), 3.04-2.88 (m, 2H), 2.78-2.57 (m, 5H), 2.51-2.39 (m, 2H), 2.39-2.30 (m, 2H), 2.29-2.10 (m, 2H), 2.10-1.95 (m, 3H). MS (ESI) m/z 348 (M+H)$^+$.

Example 16

5-methoxy-3,3-dimethyl-6-(3-(pyrrolidin-1-yl)propoxy)-3H-indol-2-amine

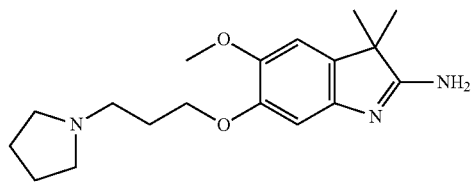 [SMILES: COc1cc2c(cc1OCCCN1CCCC1)N=C(N)C2(C)C]

5-methoxy-3,3-dimethyl-6-(3-(pyrrolidin-1-yl)propoxy)-3H-indol-2-amine was generated by the following synthetic sequence of 2 steps.

Step 1

2-(5-methoxy-2-nitro-4-(3-(pyrrolidin-1-yl)propoxy)phenyl)-2-methylpropanenitrile 2-(5-Methoxy-2-nitro-4-(3-(pyrrolidin-1-yl)propoxy)phenyl)-2-methylpropanenitrile was obtained in a similar manner to Example 6, Step 2, substituting 1-(4-(benzyloxy)-3-methoxyphenyl)cyclobutanecarbonitrile with 2-(4-(benzyloxy)-3-methoxyphenyl)-2-methylpropanenitrile. Purification by flash chromatography (silica gel, 5-20% methanol/dichloromethane) afforded 5.61 g (71%) of 2-(5-methoxy-2-nitro-4-(3-(pyrrolidin-1-yl)propoxy)phenyl)-2-methylpropanenitrile. MS (ESI) m/z 348 (M+H)$^+$.

Step 2

5-methoxy-3,3-dimethyl-6-(3-(pyrrolidin-1-yl)propoxy)-3H-indol-2-amine (21)

2-(5-Methoxy-2-nitro-4-(3-(pyrrolidin-1-yl)propoxy)phenyl)-2-methylpropanenitrile (5.61 g, 16.15 mmol), from Step 1, in AcOH (100 mL) was treated with zinc (10.56 g, 161 mmol). The reaction was stirred at 90° C. for 30 min, filtered, and concentrated to dryness. The dried residue was taken into 4:1 THF:DCM and washed with saturated aqueous sodium bicarbonate solution. Aqueous washings were back-extracted with THF:DCM mixture 5 times. Organic layers were combined, dried (MgSO4), filtered and concentrated. Purification by flash chromatography (silica gel, 15-25% 1N methanolic ammonia/dichloromethane) afforded 4.95 g (97%) of 5-methoxy-3,3-dimethyl-6-(3-(pyrrolidin-1-yl)propoxy)-3H-indol-2-amine $^1$H NMR (400 MHz, METHANOL-D4) δ 7.17 (s, 1H), 6.90 (s, 1H), 4.16 (t, J=5.5 Hz, 2H), 3.87 (s, 3H), 3.85-3.73 (m, 2H), 3.46 (t, J=7.1 Hz, 2H), 3.13 (dt, J=10.5, 7.7 Hz, 2H), 2.31-2.23 (m, 2H), 2.19 (dd, J=14.3, 7.6 Hz, 2H), 2.12-1.99 (m, 2H), 1.55 (s, 6H); MS (ESI) m/z 318 (M+H)$^+$.

Example 17

6-(3-cyclopentylpropoxy)-5-methoxy-3,3-dimethyl-3H-indol-2-amine

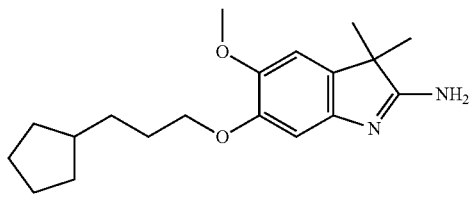 [SMILES: COc1cc2c(cc1OCCCC1CCCC1)N=C(N)C2(C)C]

6-(3-cyclopentylpropoxy)-5-methoxy-3,3-dimethyl-3H-indol-2-amine was generated by the following synthetic sequence of 4 steps.

Step 1

2-(4-(3-cyclopentylpropoxy)-3-methoxyphenyl)acetonitrile 2-(4-Hydroxy-3-methoxyphenyl)acetonitrile (0.54 g, 3.31 mmol) in THF (10 mL) was treated with 3-cyclopentylpropan-1-ol (0.424 g, 3.31 mmol), triphenylphosphine (1.128 g, 4.3 mmol) and cooled in an ice bath to 0° C. DIAD (0.785 ml, 4 mmol) was added to the reaction mixture dropwise over the period of 5 min, and the reaction was left stirring slowly warming to room temperature over 18 hours. The reaction mixture was concentrated. Purification by flash chromatography (silica gel, 0-40% EtOAc/hexanes) afforded 0.871 g (96%) of 2-(4-(3-cyclopentylpropoxy)-3-methoxyphenyl)acetonitrile. MS (ESI) m/z 274 (M+H)$^+$

Step 2

2-(4-(3-cyclopentylpropoxy)-3-methoxyphenyl)-2-methylpropanenitrile

A suspension of sodium hydride (0.16 g, 4 mmol, 60% dispersion in oil) in THF (7 mL) was cooled to 0° C. and treated slowly with 2-(4-(3-cyclopentylpropoxy)-3-methoxyphenyl)acetonitrile (0.435 g, 1.59 mmol), from Step 1, and iodomethane (0.218 mL, 3.5 mmol) in THF (3 mL). After the addition the bath was removed, and the reaction was left stirring at room temperature for 72 h. The reaction was quenched with saturated aqueous ammonium chloride, extracted with EtOAc and washed with brine. The organic layer was dried (MgSO$_4$), filtered and concentrated. Purification by flash chromatography (silica gel, 5-25% EtOAc/hexanes) afforded 0.11 g (23%) of 2-(4-(3-cyclopentylpropoxy)-3-methoxyphenyl)-2-methylpropanenitrile. MS (ESI) m/z 302 (M+H)$^+$

Step 3

2-(4-(3-cyclopentylpropoxy)-5-methoxy-2-nitrophenyl)-2-methylpropanenitrile 2-(4-(3-cyclopentylpropoxy)-3-methoxyphenyl)-2-methylpropanenitrile (0.11 g, 0.365 mmol), from Step 2, was treated in a manner analogous to 1-(4-(benzyloxy)-3-methoxyphenyl)cyclobutanecarbonitrile in Step 2 of Example 7. Purification of the crude product by flash chromatography (silica gel, 10-30% EtOAc/hexane) afforded 0.126 g (100%) of 2-(4-(3-cyclopentylpropoxy)-5-methoxy-2-nitrophenyl)-2-methylpropanenitrile. MS (ESI) m/z 347 (M+H)$^+$.

Step 4

6-(3-cyclopentylpropoxy)-5-methoxy-3,3-dimethyl-3H-indol-2-amine (22)

2-(4-(3-cyclopentylpropoxy)-5-methoxy-2-nitrophenyl)-2-methylpropanenitrile (0.126 g, 0.365 mmol), from Step 3, was treated in a manner analogous to that described for 1-(5-methoxy-2-nitro-4-(3-(pyrrolidin-1-yl)propoxy)phenyl)cyclobutanecarbonitrile in Step 5 of Example 7. Purification of the crude product by flash chromatography (silica gel, 10-30% MeOH/DCM) afforded 43 mg (37%) of 6-(3-cyclopentylpropoxy)-5-methoxy-3,3-dimethyl-3H-indol-2-amine $^1$H NMR (400 MHz, DMSO) δ 7.20 (s, 1H), 6.80 (s, 1H), 3.93 (t, J=6.5 Hz, 2H), 3.75 (s, 3H), 1.84-1.67 (m, 6H), 1.62-1.54 (m, 2H), 1.53-1.48 (m, 2H), 1.48-1.44 (m, 5H), 1.43-1.40 (m, 2H), 1.14-1.02 (m, 2H). MS (ESI) m/z 317 (M+H)$^+$.

Example 18

Determination of Inhibition of G9a Using the AlphaLISA Assay

The final compounds as described above in Examples 2-17 were tested for their inhibition of G9a. The G9a assay was conducted in an Alphascreen format to detect methyl modification of a histone H3 peptide by the histone methyl transferase activity of the G9a enzyme. A chemiluminescent signal emitted at 618 nm was generated by laser excitation of the beads at 680 nm that transfers a singlet oxygen molecule between the antibody bound donor beads specific for the methyl mark on the peptide and streptavidin bound acceptor beads that bind the biotin on the peptide.

For the assay, the following buffer was used to set up reactions: 50 mM Tris-HCl pH 7.5, 50 mM NaCl, 1 mM DTT, 0.01% Triton X-100, and 0.005% BSA, with the DTT and BSA added fresh prior to starting the reactions. The assay was set up by adding two mixtures in a 1:1 ratio; the first mixture containing 2× the concentration of G9a and the second mixture containing 2× the concentration of S-adenosyl-methionine (AK Scientific, 5018) and biotinylated-histone H3(1-21) peptide. The reactions were incubated in a humidified chamber at 25° C. for 3 hours, and subsequently quenched using the AlphaLISA anti-H3K9(me)2 acceptor beads (PerkinElmer, AL117M) and AlphaScreen streptavidin donor beads (PerkinElmer 6760002) in RIPA buffer (Sigma) at a concentration of 5 ug/ml for the donor and acceptor beads respectively and allowed to bind for 1-1.5 hours prior to detection on the Envision plate reader.

$IC_{50}$ values were calculated by fitting the inhibition percent to the concentration of inhibitor [I] in the assay in equation 1 below, to solve for the $IC_{50}$.

$$\text{Inhibition \%} = 100[I]/([I]+[IC_{50}]) \quad \text{equation 1}$$

TABLE 1

| Example | $IC_{50}$ G9a [µM] |
|---|---|
| 2 | 3.54 |
| 3 | 0.153 |
| 4 | 2.46 |
| 5 | 18.2 |
| 6 | 14.4 |
| 7 | 0.0033 |
| 8 | 0.0010 |
| 9 | 0.0050 |
| 10 | 0.150 |
| 11 | 0.754 |
| 12 | 0.0037 |
| 13 | 0.0048 |
| 14 | 1.342 |
| 15 | 0.018 |
| 16 | 0.0009 |
| 17 | 12.9 |

All compounds tested exhibited inhibition of G9a in a range from about 0.001 to 18.2 uM. Importantly, they all demonstrated inhibitory activity of G9a.

Example 19

Cellular Immunostaining (In-Cell Western)

The compound of Example 7 (5'-methoxy-6'-(3-(pyrrolidin-1-yl)propoxy)spiro[cyclobutane-1,3'-indol]-2'-amine; hereinafter "the compound of Example 7") was used to probe the function of G9a in cells. An In-Cell Western assay (H3K9Me2 antibody immunofluorescence) was performed after treating a human prostate cancer cell line, PC3, with the compound of Example 7 for 72 hours. For comparison, the known G9a inhibitor UNC0638 (see structure in FIG. 1) was evaluated in this study concurrently.

The assay was performed as follows:

Human PC3 cells (ATCC, Manassas, Va.) were grown in RPMI+10% Fetal Bovine Serum and plated at 5,000 cells per well in a 96-well plate. The following day compounds and DMSO controls were added in triplicate at the indicated concentrations. Cells were fixed following incubation at 37° C. for 72 hours with 10% formaldehyde and then permeabilized with 0.1% Triton X-100. Cells were then washed with PBS and blocked with 0.1% BSA/PBS solution. Mouse anti-H3K9me2 (1:200, AbCam #1220, Cambridge, Mass.) and rabbit anti-Histone H3 (1:500, Cell Signaling Technology #4499, Danvers, Mass.) primary antibodies in 0.3% BSA were then added together to each well and incubated overnight at 4° C. The following day cells were washed in PBS-T (PBS with 0.1% Tween) followed by addition of anti-mouse (IR800) and anti-rabbit (IR700) secondary antibodies (LI-COR Biosciences, Lincoln, Nebr.) and incubated for one hour at room temperature. Cells were then washed with PBS-T followed by PBS and liquid was removed from all wells. The plate was scanned using both the 700 nm (anti-rabbit detection) and 800 nm (anti-mouse detection) channels on the Odyssey Imaging System (LI-COR Biosciences, Lincoln, Nebr.). Data was quantified using the LI-COR imaging suite and graphed as % inhibition H3K9me2/total H3/well compared to DMSO control wells. Wells treated in triplicate were averaged for each indicated concentration and error bars represent the standard deviation (n=3).

TABLE 2

H3K9me2 Inhibition (UNC0638)
UNC0638

| concentration (uM) | % inhibition | | | average | standard deviation |
|---|---|---|---|---|---|
| 3 | 47.82637 | 48.21973 | 49.37809 | 48.47473 | 0.8066737 |
| 1 | 44.89697 | 43.20971 | 47.35147 | 45.15272 | 2.0826906 |
| 0.3 | 41.09843 | 41.04708 | 40.37287 | 40.83946 | 0.4048942 |
| 0.1 | 24.5866 | 27.67757 | 25.02562 | 25.76327 | 1.6723076 |
| 0.03 | 10.04232 | 17.8107 | 15.8006 | 14.55121 | 4.0320805 |

TABLE 3

H3K9me2 Inhibition (Example 7)
Example 7

| concentration (uM) | % inhibition | | | average | standard deviation |
|---|---|---|---|---|---|
| 3 | 45.902 | 47.77479 | 48.92418 | 47.53366 | 1.5254511 |
| 1 | 44.15787 | 43.83296 | 45.11364 | 44.36816 | 0.6657318 |
| 0.3 | 36.55683 | 34.46786 | 40.34597 | 37.12355 | 2.9797514 |
| 0.1 | 20.57829 | 24.63036 | 27.83145 | 24.3467 | 3.6348886 |
| 0.03 | 10.82461 | 15.08395 | 10.18314 | 12.03057 | 2.6636898 |

Figure 2:
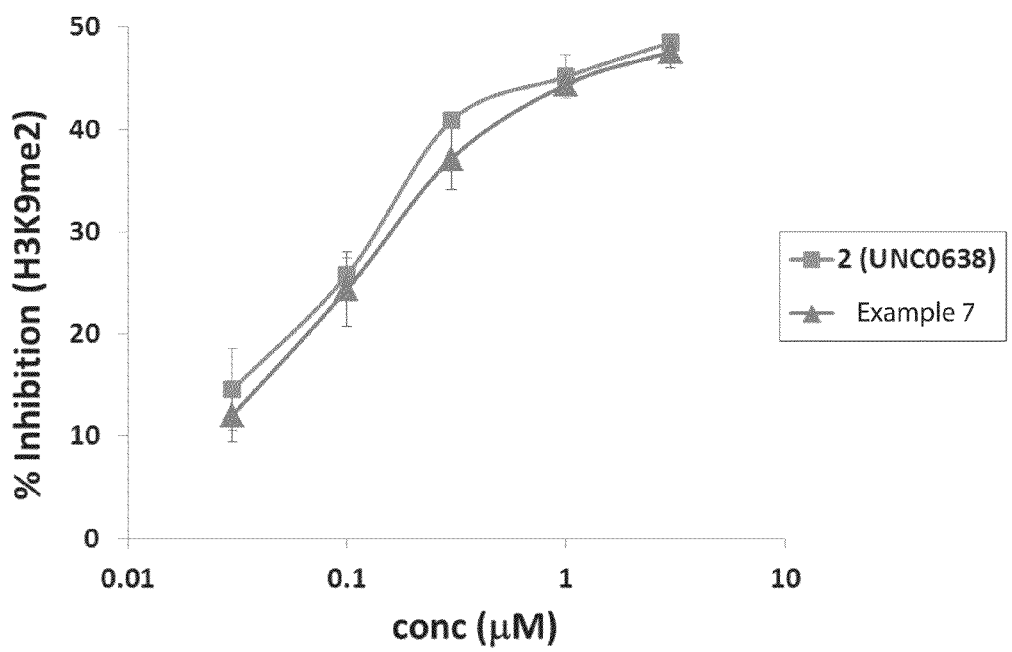
FIG. 2 is a graph illustrating the reduction of cellular levels of H3K9me2 with the compound of Example 7 and UNC0638.
Figure 11:
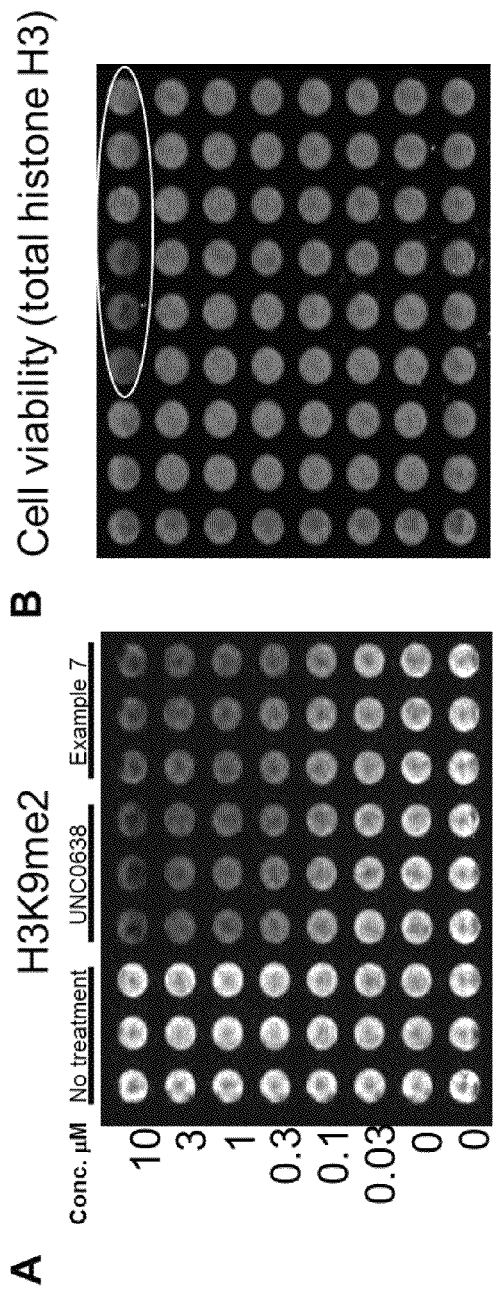
FIG. 11 is a series of two pictures that depict (A) the reduction of H3K9me2 levels in PC3 cells treated with the compound of Example 7 and UNC0638; and (B) cell viability of PC3 cells treated with the compound of Example 7 and UNC0638.

The results of the assay demonstrated that the cellular levels of H3K9Me2 were reduced by nearly 50% at 3 µM for both compounds (FIGS. 2 and 11A and Tables 2 and 3). No difference in cell viability as measured by total histone H3 was observed between no treatment, cells treated with UNC0638, and the compound of Example 7 (FIG. 11B).

Figure 12:
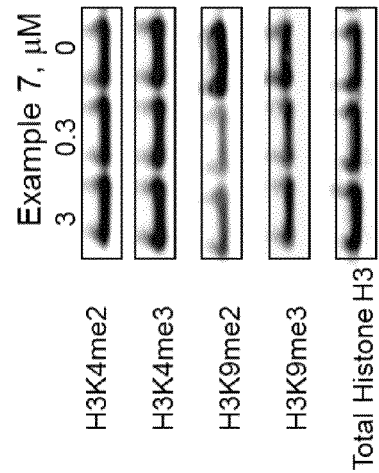
FIG. 12 is a western blot assay depicting the effect of the compound of Example 7 on H3K9me2 in PC3 treated cells.

In addition, the levels of total histone 3, H3K27Me3, H3K36Me2 H3K4me2, H3K4me3, and H3K9me3 were unaltered in cells treated under similar conditions, confirming that the observed effect of these inhibitors was H3K9 specific (FIGS. 2 and 12). In summary, these data demonstrated that the compound of Example 7 inhibited H3K9 dimethylation within treated cells in a specific manner.

Example 20

X-ray Co-crystal Structure of the Compound of Example 6 with G9a

A high-resolution X-ray co-crystal structure of the compound of Example 7 with G9a was obtained, showing the interactions between the lysine channel of G9a and the compound of Example 7. Specifically, the binding to the substrate peptide site on G9a involved a mix of both hydrophobic and electrostatic interactions (FIG. 3). The sidechain of L1086 formed the hydrophobic wall of the pocket and was in Van der Waals contact with the phenyl group of the compound of Example 7. The methoxy moiety of the ligand sat in a hydrophobic dimple formed by the sidechains of F1158, I1161, and the aliphatic portion of K1162.

The amidine nitrogen atoms of the compound of Example 7 formed electrostatic hydrogen bonds with the sidechain carboxylates of D1074, and D1088. In addition, the pyrrolidine nitrogen donated a hydrogen to the backbone carbonyl of L1086 while the carbon atoms of the pyrrolidine sat in a hydrophobic sub-pocket formed by the sidechains of Y1067, F1087, F1152, Y1154, and F1158. This position of the pyrrolidine forced the two central methylene carbons of the four atom linker between the pyrrolidine and phenyl into a gauche conformation.

The sidechain of R1157, well-ordered in the structure, packed against the face of the bound ligand opposite that of L1086 in a parallel fashion. The guanidine moiety of this arginine formed electrostatic hydrogen bonds to the sidechain carboxylates of D1074 and D1088. The overall binding mode of the compound of Example 7 was similar to that previously observed for UNC0638.

Example 21

Differentiation of MV4;11 Cells by a G9a Inhibitor

As described above, the compound of Example 7 inhibited H3K9 methylation within cells. To further examine the effect of the compound of Example 7 on cells, differentiation of MV4;11 cells was examined in the presence of the compound of Example 7 or all trans retinoic acid. MV4;11 cells are a human acute myelocytic leukemia (AML) cell line derived from a human male with leukemia.

Figure 4A:
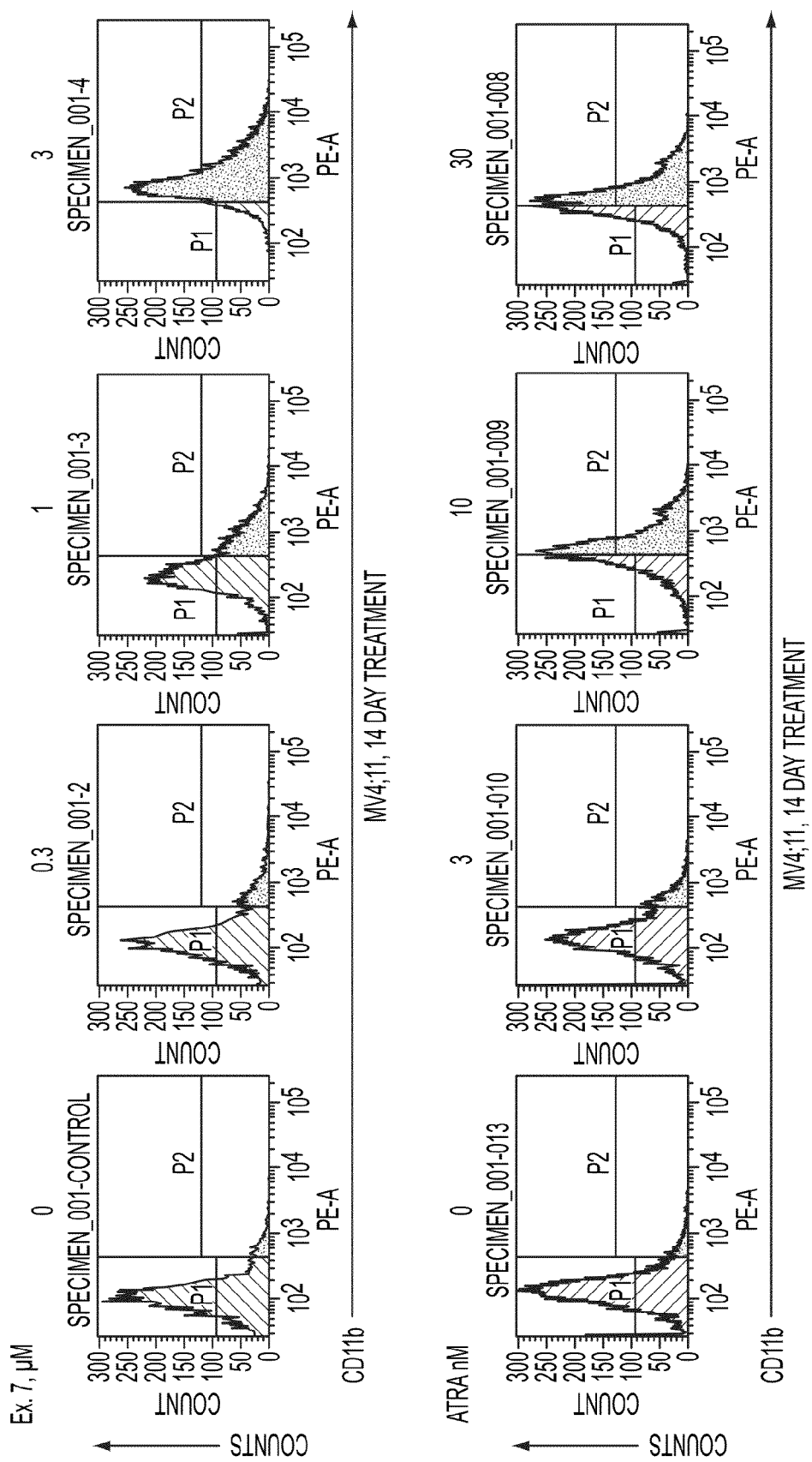
FIG. 4 is a series of pictures showing (A) FACS analysis of MV4;11 cells upon treatment with the compound of Example 7 and ATRA; (B) cell viability and cell proliferation of MV4; 11 cells upon treatment with the compound of Example 7 and ATRA; (C) cell cycle analysis of the MV4;1 cells; and (D) Wright-Giemsa staining of MV4;11 cells treated with DMSO or the compound of Example 7.

Specifically, MV4;11 cells were incubated with 0 µM, 0.3 µM, 1 µM, or 3 µM of the compound of Example 7 or all trans retinoic acid (ATRA) for 14 days. Cells were then fixed, stained with an anti-CD11b antibody and analyzed by flow cytometry as shown in FIG. 4A. These data demonstrated that as the concentration of the compound of Example 7 or ATRA increased, more cells in the population expressed the marker CD11b, which indicated differentiation of the MV4;11 cells.

Figure 4B:
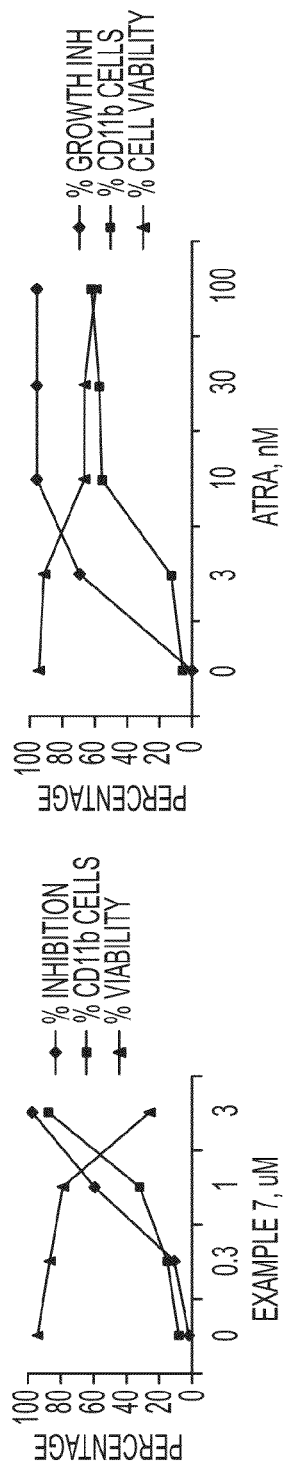

The MV4;11 cells were additionally assayed for cell proliferation (CellTiter Glo) and viability (trypan blue exclusion) following treatment with the compound of Example 7 or ATRA for 14 days (FIG. 4B). As the concentration of the compound of Example 7 increased, cell viability decreased while inhibition of cellular proliferation increased. At 3 µM of the compound of Example 7, about 20% of the MV4;11 cells were viable and about 100% of the MV4;11 cells no longer proliferated. Additionally, as the concentration of the compound of Example 7 increased, more cells in the population expressed the differentiation marker CD11b (i.e., at 3 µM, about 90% of the cells were positive for CD11b). In contrast, ATRA had less of an effect on cell viability, but also lead to growth inhibition and expression of CD11b as the concentration of ATRA increased.

Figure 4C:
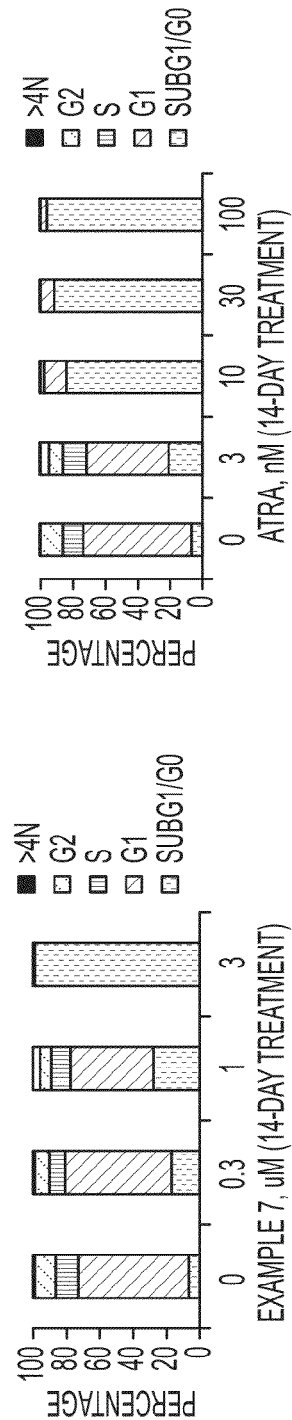
Figure 4D:
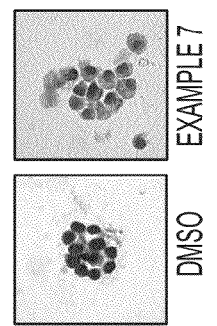

Cell cycle analysis (PI staining) of MV4;11 cells following treatment with the compound of Example 7 or ATRA for 14 days at the indicated concentrations (i.e., 0 µM, 03 µM, 1 µM, and 3 µM) is illustrated in FIG. 4C, while FIG. 4D demonstrates Wright-Giemsa staining of MV4;11 cells treated with DMSO or 5 mM of the compound of Example 7 for 10 days. The cell cycle analysis data indicated that as the concentration of the compound of Example 7 or ATRA increased, more cells were observed to be in the subG1/G0 phase of the cell cycle (FIG. 4C), and thus, arrested.

Overall these results showed that the compound of Example 7 induced differentiation and affected the viability of MV4;11 cells. Importantly, the compound of Example 7 impacted cell growth and induced cell differentiation in these leukemia cells. These results also indicated that sustained reduction of H3K9me2 in tumors was required to observe anti-proliferation effects.

Example 22

Figure 5:
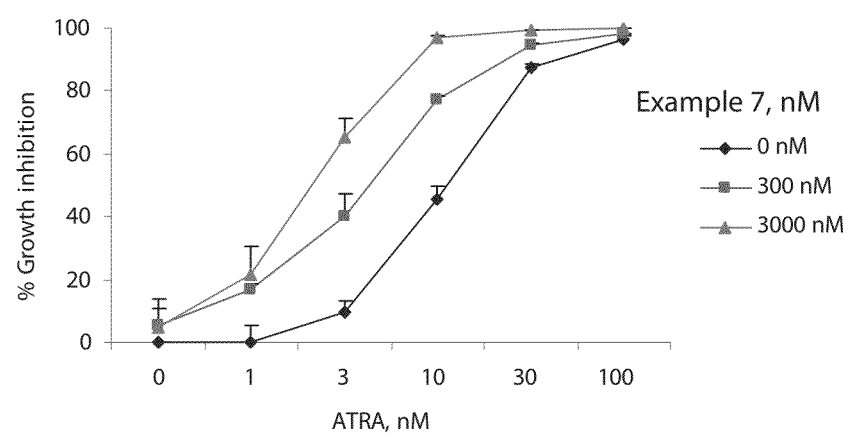
FIG. 5 is a graph depicting growth inhibition curves of MV4;11 cells treated with the compound of Example 7 and ATRA, alone and in combination.

Effect of the Combination of a G9a Inhibitor and all Trans Retinoic Acid (ATRA) on MV4;11 Cells MV4;11 cells were treated with 0, 300 nM, or 3 µM of the compound of Example 7 in combination with 0, 1 nM, 3 nM, 10 nM, 30 nM, and 100 nM concentrations of All trans retinoic acid (ATRA) for 5 days. Cellular proliferation was determined by CellTiter Glo assay. FIG. 5 illustrates the results of this study, showing that the combination of the compound of Example 7 and ATRA had additive effects on MV4;11 proliferation. These results demonstrated that this additive anti-leukemic effect was superior to treatment with either compound alone.

Example 23

Differentiation and Viability of HL-60 Cells Treated with a G9a Inhibitor

Figure 6A:
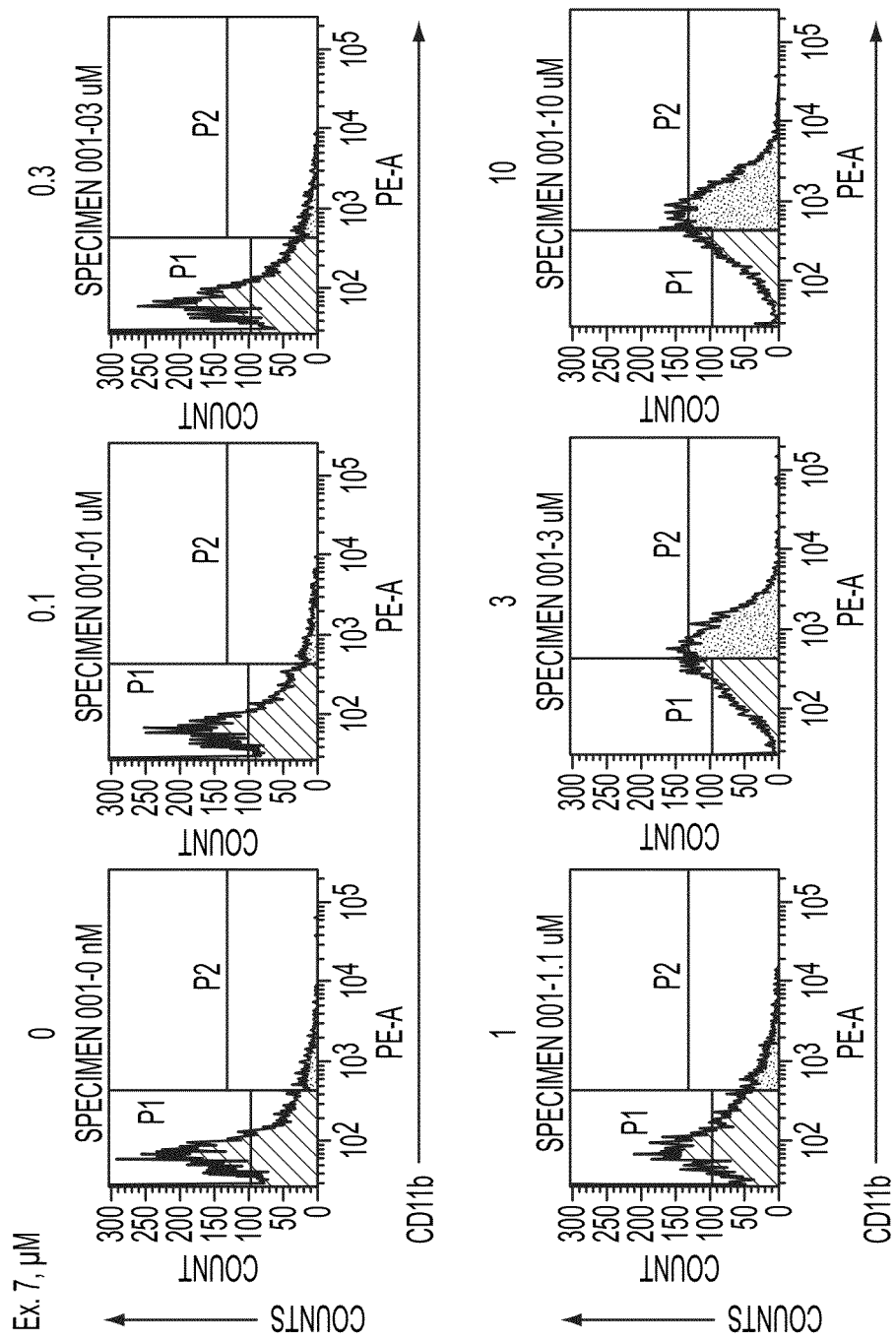
FIG. 6 is a series of pictures showing (A) FACS analysis of HL-60 cells upon treatment with the compound of Example 7; (B) cell viability and cell proliferation of MV4;11 cells upon treatment with the compound of Example 7; (C) and cell cycle analysis of the MV4;1 cells.

To further examine the effect of the compound of Example 7 on the differentiation and viability of leukemia cells, HL-60 acute promyelocytic cells (HL-60 cells) were treated with the compound of Example 7. Specifically, HL-60 cells were incubated with 0, 0.1 µM, 0.3 µM, 1 µM, 3 µM, and 10 µM concentrations of the compound of Example 7 for 4 days. Cells were then fixed, stained with an anti-CD11b antibody and analyzed by flow cytometry (FIG. 6A). As observed above in Example 23 with MV4;11 cells, the compound of Example 7 induced differentiation of the HL-60 cells as evidenced by increased numbers of cells expressing the differentiation marker CD11b as the concentration of the compound of Example 7 increased.

Figure 6B:
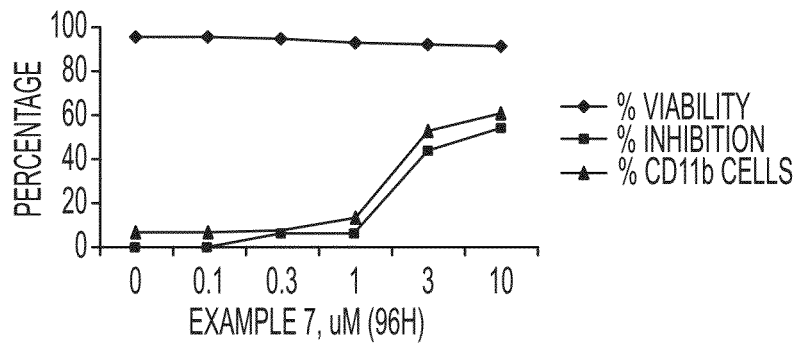

The HL-60 cells from were additionally assayed for cell proliferation (CellTiter Glo) and viability (trypan blue exclusion) following the 4 day treatment with the compound of Example 7 (FIG. 6B). HL-60 cells were exposed to the following concentrations of the compound of Example 7: 0 µM, 0.1 µM, 0.3 µM, 1 µM, 3 µM, and 10 µM. As the concentration of the compound of Example 7 increased, cell viability was largely unaffected, but both inhibition of proliferation and cells expressing CD11b increased.

Figure 6C:
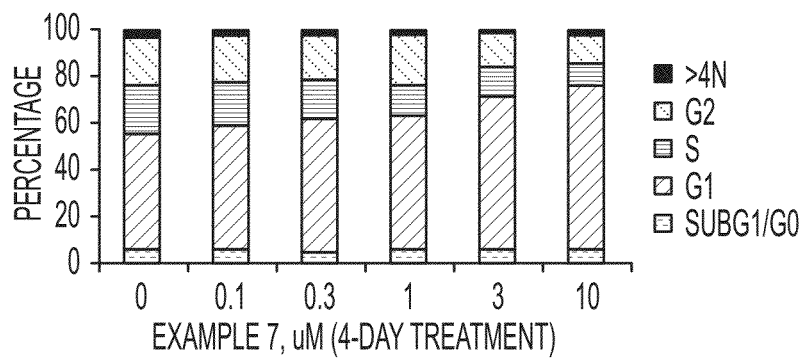

Cell cycle analysis (PI staining) of HL-60 cells following the 4 day treatment at the indicated concentrations (i.e., 0 µM, 0.1 µM, 0.3 µM, 1 µM, 3 µM, and 10 µM) was also performed (FIG. 6C). As the concentration of the compound of Example 7 increased, increased numbers of cells were in the G1 phase of the cell cycle, indicating arrest.

In summary, the results from these experiments demonstrated that the compound of Example 7 induced differentiation of HL-60 cells, but did not affect the viability of the HL-60 acute promyelocytic cell line. These data also demonstrated that the compound of Example 7 inhibited proliferation of the HL-60 cells.

Example 24

Viability of PBMCs Treated with G9a Inhibitors

Figure 7:
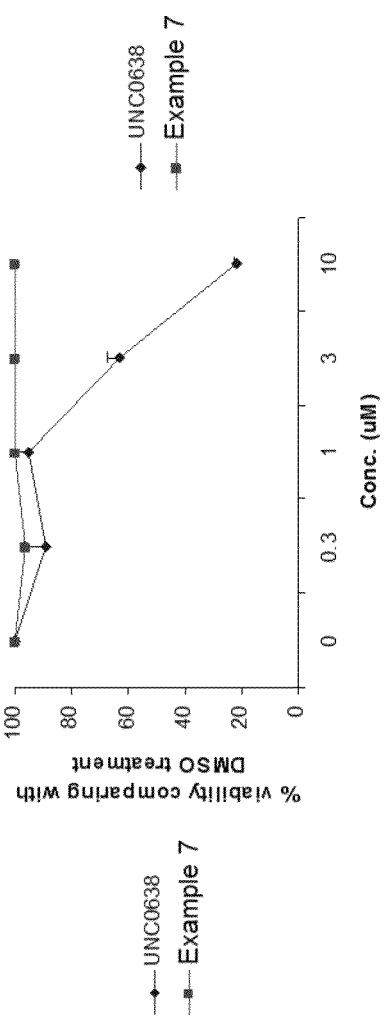
FIG. 7 is a series of 2 graphs depicting (A) caspace 3/7 activity and (B) cell viability of PBMCs treated with the compound of Example 7 and UNC0638.
Figure 7:
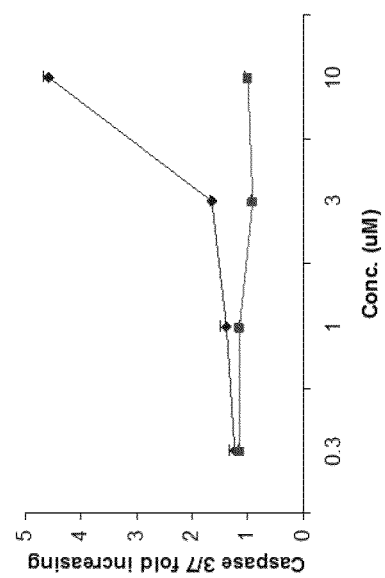

To further examine the effect of the compound of Example 7 on cell viability (i.e., cytotoxicity), human peripheral blood mononucleated cells (PBMCs) were incubated with 0, 0.1 uM, 0.3 uM, 1 uM, 3 uM, and 10 uM concentrations of the compound of Example 7 or UNC0638 for 48 h. Following treatment, Caspase 3/7 activity (i.e., a marker of apoptosis) was assessed by the Caspase-Glo 3/7 assay system (FIG. 7A), and cell viability was assessed by CellTiter Glo assay (FIG. 7B). In both experiments, the compound of Example 7 displayed no effect on cell viability, while UNC0638 did at higher concentrations. Accordingly, these data indicated that the compound of Example 7, unlike another G9a inhibitor UNC0638, was not cytotoxic to PBMCs.

Example 25

PK/PD Study with a G9a Inhibitor

Figure 8:
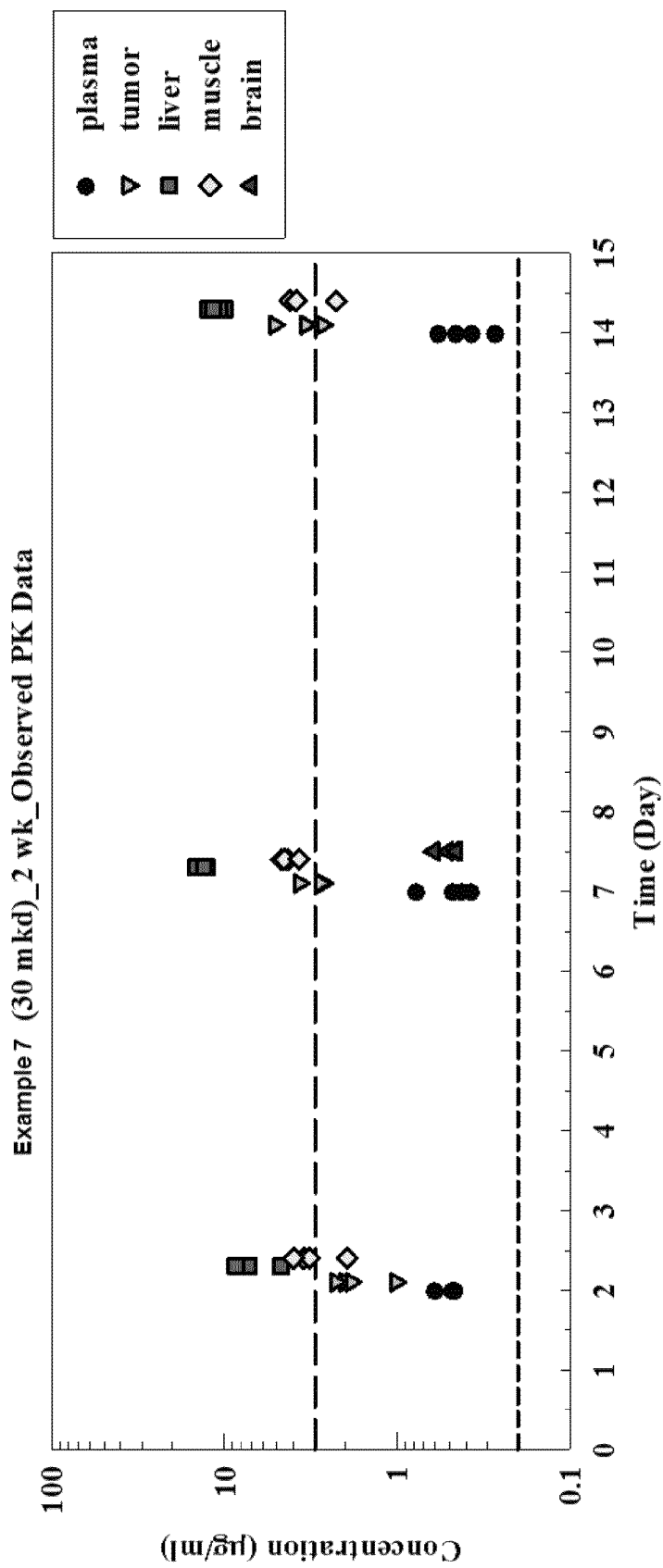
FIG. 8 is a chart illustrating the concentrations of the compound of Example 7 found in various tissue types after administration to tumored mice.

To examine the efficacy of the compound of Example 7, mice with implanted leukemia cells were exposed to the compound of Example 7 after establishment of the tumor. Specifically, subcutaneous MV4;11 xenografts were implanted in SCID/bg mice and allowed to grow to 200 mm$^3$. The compound of Example 7 was administered at 30 mg/kg/day to the mice by osmotic mini-pump for 14 days. Plasma and tissue (i.e., tumor, liver, muscle and brain) samples were collected at 2, 7, and 14 days after administration of the compound of Example 7 and analyzed for concentrations of the compound of Example 7 as well as the reduction in H3K9me2 relative to vehicle treated mice. FIG. 8 illustrates the concentrations of the compound of Example 7 found in the listed tissue types. Table 4 reports the reduction in H3K9me2. These results demonstrated a significant accumulation of the compound of Example 7 in tumor tissue (as well as liver and muscle tissue), and a cumulative effect on reduction of H3K9me2 with continuous dosing of the G9a inhibitor. In particular, by day 14, dimethylation of lysine 9 of histone H3 in the tumor tissue was reduced by 46 percent as compared to the vehicle. In summary, these data demonstrated that the compound of Example 7 accumulated in the tumor tissue and achieved a reduction in dimethylation of H3K9 that increased with dosing.

TABLE 4

| Day | reduction in H3K9me2 |
|---|---|
| 2 | 0% |
| 7 | 25% |
| 14 | 46% |

Example 26

In vivo Efficacy Study with a G9a Inhibitor

Figure 9:
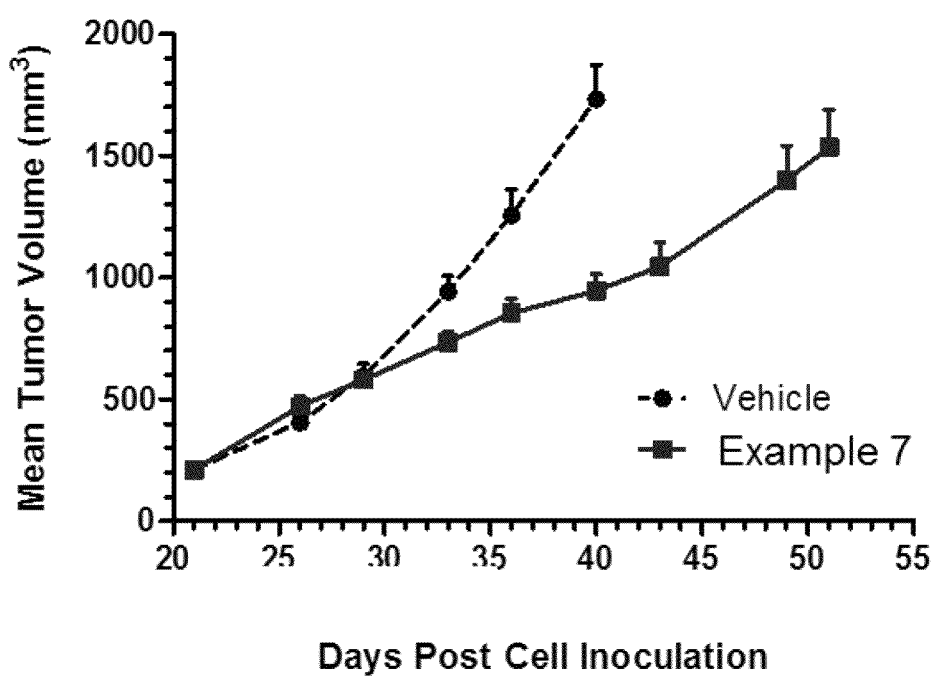
FIG. 9 is a graph depicting tumor growth of mice treated with the compound of Example 7 and vehicle treated mice.

The efficacy of the compound of Example 7 was further examined by monitoring tumor volume during treatment with the compound of Example 7. Subcutaneous MV4;11 xenografts were implanted in SCID/bg mice and allowed to grow to 200 mm$^3$. The compound of Example 7 was then administered to the mice at 30 mg/kg/day by osmotic mini-pump for 14 days. Tumors were measured at the indicated time points (i.e., from 20 days to 55 days post-inoculation of the mice with the MV4;11 cells) and tumor growth was plotted as a function of time (FIG. 9). Tumor volume was measured in mm$^3$ and these results in FIG. 9 demonstrated a growth inhibition of the tumors after dosing with the compound of Example 7 (filled square) as compared to the vehicle (filled circle).

Example 27

Cytotoxicity of G9a Inhibitors

The cytotoxicity of the compound of Example 7, in comparison to UNC0638 was investigated. Table 5 reports IC50 values for the compound of Example 7 and UNC0638 in a panel of tumor cell lines as determined by CellTiter Glo assay.

Figure 10:
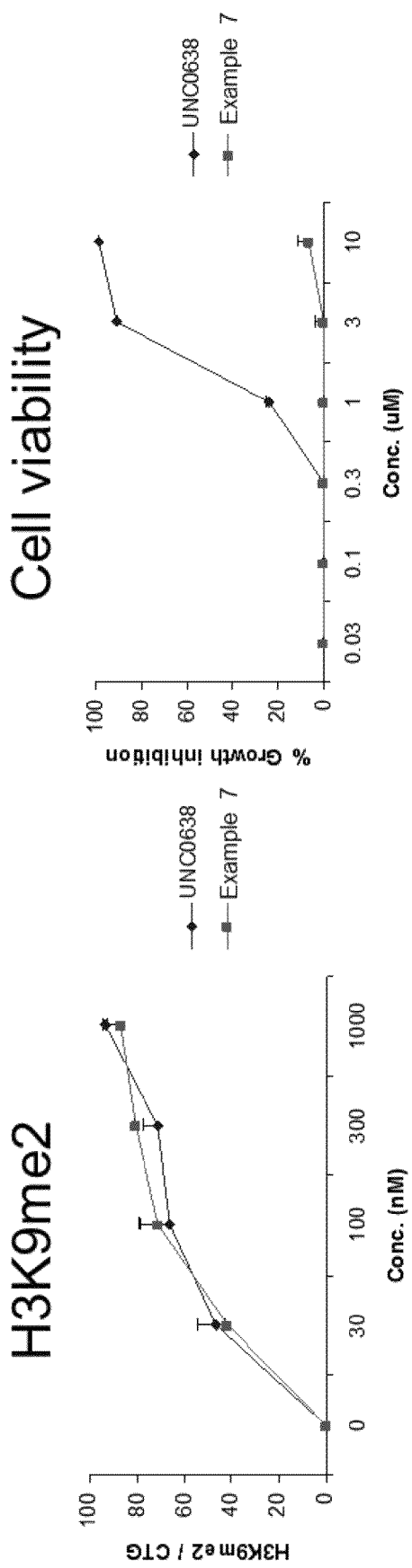
FIG. 10 is a series of 2 graphs showing (left panel) the relationship between the amount of G9a inhibitor added and H3K9me2 reduction in HT1080 cells; and (right panel) cell viability of HT1080 cells upon treatment with the compound of Example 7 and UNC0638.

In addition, H3K9me2 levels by the AlphaLISA assay system were determined following 48 h treatment of HT1080 fibrosarcoma cells with the compound of Example 7 and UNC0638 at concentrations of 0, 30 nM, 100 nM, 300 nM, and 1,000 nM (FIG. 10, left panel). Cell viability of HT1080 fibrosarcoma cells was also determined after 48 h treatment with the compound of Example 7 and UNC0638 at concentrations of 0, 30 nM, 100 nM, 300 nM, 1,000 nM, 3,000 nM, and 10,000 nM (FIG. 10, right panel). The results of these experiments demonstrated that the compound of Example 7 showed reduced cytotoxicity in HT1080 fibrosarcoma cells as compared to UNC0638 despite equivalent effects on H3K9me2 reduction. Accordingly, the compound of Example 7 had significantly less cytotoxic effects on the growth of a solid tumor cell line (i.e., HT1080 fibrosarcoma cells) as compare to another G9a inhibitor, namely UNC0638.

TABLE 5

Cytotoxicity of the Example 7 compound and UNC0368

| Cell line | Example 7 compound (IC50 uM) | UNC0368 (IC50 uM) |
|---|---|---|
| 7-day proliferation, neural crest derived lines | | |
| MHH-65-1 | >10 | 1.9 |
| CAPO-ES1 | >10 | 1.2 |
| PA-1 | >10 | 0.2 |
| SK-N-MC | 9.7 | 0.2 |
| G-401 | >10 | 0.4 |
| ZR7350 | >10 | 1.2 |
| US2OS | >10 | 0.5 |
| DaoY | >10 | 0.1 |
| PH-1 | >10 | 4.4 |
| TC-71 | >10 | 0.6 |
| 12-day proliferation, neural crest derived lines | | |
| IMR-32 | >10 | 0.1 |
| A-201 | >10 | 0.6 |
| 5-day proliferation | | |
| THP-1 | >10 | 4.9 |
| RS4; 11 | >10 | 3.1 |
| RPMI8226 | >10 | 5.1 |
| OPM2 | >10 | 5.6 |
| L-363 | >10 | 3.9 |
| KMS12 | >10 | 4.4 |
| KMS11 | >10 | 4 |
| Kasume-1 | >10 | 1.1 |
| HL-60 | >10 | 6.5 |
| H929 | >10 | 4.6 |
| MV4; 11 | >10 | 1.7 |
| K562 | >10 | 5.3 |
| 22RV1 | >10 | 0.2 |
| Calu6 | >10 | 0.5 |
| DU145 | >10 | 0.7 |
| LN229 | >10 | 0.5 |
| LNCap | >10 | 0.3 |
| SKBR3 | >10 | 0.6 |

In summary, the above data in Examples 18-27 demonstrated that the compound of Example 7 was an inhibitor of G9a and GLP. Additionally, the compound of Example 7 displayed minimal cytotoxicity and did not impact the viability of PBMCs. The compound of Example 7 also had significantly reduced cytotoxicity on the growth of solid tumor cell lines as compared to another G9a inhibitor. The compound of Example 7 further inhibited the proliferation of leukemia cells lines and this inhibition was increased in the presence of ATRA.

What is claimed is:

1. A compound of formula (I)

$$\text{(I)}$$

or a pharmaceutically acceptable salt thereof,
wherein
$R^1$ and $R^2$ are each independently selected from the group consisting of alkyl, and haloalkyl, or $R^1$ and $R^2$ together form an optionally substituted 3- to 6-membered cycloalkyl;
$R^3$ is selected from the group consisting of hydrogen, alkyl, alkylalkoxy, alkylamino, and haloalkyl;
$R^4$ is selected from the group consisting of hydrogen, $OR^a$, $SR^a$, $NR^bR^c$, haloalkyl, and alkyl, wherein alkyl is optionally substituted with halogen, haloalkyl, alkyl, aminoalkyl, alkoxy, cycloalkyl, aryl, heterocycle, and heteroaryl, wherein cycloalkyl, aryl, heterocycle, and heteroaryl are optionally substituted with alkyl, halogen, and haloalkyl;
$R^a$ is haloalkyl, cycloalkyl, or alkyl, wherein alkyl is optionally substituted with halogen, haloalkyl, alkyl, amino, aminoalkyl, alkoxy, cycloalkyl, aryl, heterocycle, and heteroaryl, wherein cycloalkyl, aryl, heterocycle, and heteroaryl are optionally substituted with alkyl, halogen, and haloalkyl;
$R^b$ and $R^c$ are each independently haloalkyl, cycloalkyl, or alkyl, wherein alkyl is optionally substituted with halogen, haloalkyl, alkyl, aminoalkyl, alkoxy, cycloalkyl, aryl, heterocycle, and heteroaiyl, wherein cycloalkyl, aryl, heterocycle, and heteroaryl are optionally substituted with alkyl, halogen, and haloalkyl; or $R^b$ and $R^c$ together form an optionally substituted 3- to 6-membered heterocycle.

2. The compound of claim 1, wherein $R^4$ is $OR^a$.

3. The compound of claim 2, wherein $R^a$ is alkyl optionally substituted with cycloalkyl, heterocycle, and heteroaryl, wherein cycloalkyl, heterocycle, and heteroaryl are optionally substituted with alkyl and halogen.

4. The compound of claim 2, wherein $R^a$ is alkyl substituted with heterocycle, wherein heterocycle is optionally substituted with alkyl and halogen.

5. The compound of claim 4, wherein $R^3$ is alkyl.

6. The compound of claim 5, wherein $R^1$ and $R^2$ are independently alkyl.

7. The compound of claim 5, wherein $R^1$ and $R^2$ together form an optionally substituted 3- to 6-membered cycloalkyl.

8. The compound of claim 1, wherein $R^1$ and $R^2$ are independently alkyl.

9. The compound of claim 1, wherein $R^1$ and $R^2$ together form an optionally substituted 3- to 6-membered cycloalkyl.

10. The compound of claim 1 selected from the group consisting of:
  5',6'-dimethoxyspiro[cyclobutane-1,3'-indol]-2'-amine;
  5',6'-dimethoxyspiro[cyclopentane-1,3'-indol]-2'-amine;
  5',6'-dimethoxyspiro[cyclohexane-1,3'-indol]-2'-amine;
  5'-methoxyspiro[cyclobutane-1,3'-indol]-2'-amine;
  5'-methoxy-6'-(3-(pyrrolidin-1-yl)propoxy)spiro[cyclobutane-1,3'-indol]-2'-amine;
  5'-methoxy-6'-((1-methylpyrrolidin-3-yl)methoxy)spiro[cyclobutane-1,3'-indol]-2'-amine;
  5'-methoxy-6'-((1-methylpyrrolidin-2-yl)methoxy)spiro[cyclobutane-1,3'-indol]-2'-amine;
  5'-methoxy-6'-(2-(1-methylpyrrolidin-2-yl)ethoxy)spiro[cyclobutane-1,3'-indol]-2'-amine;
  6'-(3-(3-fluoroazetidin-1-yl)propoxy)-5'-methoxyspiro[cyclobutane-1,3'-indol]-2'-amine;
  6'-(3-(3,3-difluoroazetidin-1-yl)propoxy)-5'-methoxyspiro[cyclobutane-1,3'-indol]-2'-amine;
  6'-(3-(1H-imidazol-1-yl)propoxy)-5'-methoxyspiro[cyclobutane-1,3'-indol]-2'-amine;
  (S)-6'-(3-(3-fluoropyrrolidin-1-yl)propoxy)-5'-methoxyspiro[cyclobutane-1,3'-indol]-2'-amine;
  (R)-6'-(3-(3-fluoropyrrolidin-1-yl)propoxy)-5'-methoxyspiro[cyclobutane-1,3'-indol]-2'-amine;
  5-methoxy-3,3-dimethyl-6-(3-(pyrrolidin-1-yl)propoxy)-3H-indol-2-amine; and
  6-(3-cyclopentylpropoxy)-5-methoxy-3,3-dimethyl-3H-indol-2-amine,
or a pharmaceutically acceptable salt thereof.

11. A pharmaceutical composition comprising a therapeutically effective amount of the compound of claim 1 or a pharmaceutically acceptable salt thereof, in combination with one or more pharmaceutically acceptable carriers.

* * * * *